US012594411B2

(12) United States Patent
Subramanian et al.

(10) Patent No.: US 12,594,411 B2
(45) Date of Patent: Apr. 7, 2026

(54) APPARATUS AND METHOD FOR JOINING METAL SLEEVE ONTO A TUBE

(71) Applicant: BEST MEDICAL INTERNATIONAL, INC., Springfield, VA (US)

(72) Inventors: Manny R. Subramanian, Frederick, MD (US); Rashmi M Amin, Springfield, VA (US); Stephen Bettencourt, Warren, RI (US)

(73) Assignee: Best Medical International, Inc., Springfield, VA (US)

( * ) Notice: Subject to any disclaimer, the term of this patent is extended or adjusted under 35 U.S.C. 154(b) by 96 days.

(21) Appl. No.: 15/682,429

(22) Filed: Aug. 21, 2017

(65) Prior Publication Data

US 2019/0054286 A1      Feb. 21, 2019

(51) Int. Cl.
A61M 39/10          (2006.01)
A61M 25/00          (2006.01)
(Continued)

(52) U.S. Cl.
CPC .... A61M 39/1055 (2013.01); A61M 25/0014 (2013.01); A61M 39/12 (2013.01);
(Continued)

(58) Field of Classification Search
CPC .......... A61M 39/1055; A61M 2207/10; A61M 2039/0009; A61M 39/12; B23K 20/12
(Continued)

(56) References Cited

U.S. PATENT DOCUMENTS

| 3,134,278 | A | * | 5/1964 | Hollander | .............. | B23K 20/12 |
| | | | | | | 228/114.5 |
| 3,469,579 | A | | 9/1969 | Hubert | | |

(Continued)

FOREIGN PATENT DOCUMENTS

| BE | 1002911 A3 | | 7/1991 | | |
| CN | 201848997 | * | 6/2011 | ............. | B29G 65/18 |

(Continued)

OTHER PUBLICATIONS

PCT Application No. PCT/US18/47041, International Search Report, Nov. 5, 2018, 13 pages.
(Continued)

*Primary Examiner* — Seahee Hong

(57) ABSTRACT

A process, apparatus and a catheter and a flexi needle for medical applications formed by the process of selecting a tubular flexible member and a metal/ceramic cap member to be securely joined to the tubular member, placing the cap member in engaging relation with a holding member of a material joining device, securing the tubular member on a positioning member of the material joining device, positioning a distal end of the tubular member in engaging relation with an end of the cap member positioned in the holding member, and rotating the holding member and maintaining the tubular member in frictionally engaging relation with the cap member to melt or soften a predetermined portion of the distal end of the tubular member engaged with the cap member to integrally join a predetermined portion of the distal end of the tubular member within the cap member forming a joined composite member.

25 Claims, 14 Drawing Sheets

(51) Int. Cl.

| | |
|---|---|
| *A61M 39/12* | (2006.01) |
| *A61M 39/20* | (2006.01) |
| *B29C 48/00* | (2019.01) |
| *B29C 48/09* | (2019.01) |
| *B29C 48/32* | (2019.01) |
| *B29C 65/00* | (2006.01) |
| *B29C 65/06* | (2006.01) |
| *B29C 65/44* | (2006.01) |
| *B29C 65/46* | (2006.01) |
| *B29C 65/56* | (2006.01) |
| *B29C 65/64* | (2006.01) |
| *B29C 65/72* | (2006.01) |
| *B29C 65/78* | (2006.01) |
| *A61M 39/00* | (2006.01) |
| *B29K 96/04* | (2006.01) |
| *B29L 31/00* | (2006.01) |

(52) U.S. Cl.
CPC ......... *A61M 39/20* (2013.01); *B29C 48/0021* (2019.02); *B29C 48/022* (2019.02); *B29C 48/09* (2019.02); *B29C 48/32* (2019.02); *B29C 65/0672* (2013.01); *B29C 65/44* (2013.01); *B29C 65/46* (2013.01); *B29C 65/561* (2013.01); *B29C 65/645* (2013.01); *B29C 65/72* (2013.01); *B29C 65/7817* (2013.01); *B29C 65/7832* (2013.01); *B29C 65/7838* (2013.01); *B29C 65/7841* (2013.01); *B29C 66/1122* (2013.01); *B29C 66/3032* (2013.01); *B29C 66/522* (2013.01); *B29C 66/53241* (2013.01); *B29C 66/5344* (2013.01); *B29C 66/612* (2013.01); *B29C 66/73116* (2013.01); *B29C 66/73118* (2013.01); *B29C 66/7392* (2013.01); *B29C 66/742* (2013.01); *B29C 66/7461* (2013.01); *B29C 66/8322* (2013.01); *A61M 2025/0034* (2013.01); *A61M 2039/0009* (2013.01); *A61M 2207/10* (2013.01); *B29C 66/71* (2013.01); *B29C 66/7426* (2013.01); *B29C 66/7428* (2013.01); *B29C 66/74281* (2013.01); *B29C 66/74283* (2013.01); *B29C 66/74285* (2013.01); *B29K 2096/04* (2013.01); *B29K 2995/0056* (2013.01); *B29L 2031/7542* (2013.01); *B29L 2031/7544* (2013.01)

(58) Field of Classification Search
USPC ................. 29/237, 238, 240; 228/112, 114.5
See application file for complete search history.

(56) References Cited

U.S. PATENT DOCUMENTS

| | | | | |
|---|---|---|---|---|
| 3,888,405 A | * | 6/1975 | Jones ................... | B23K 20/121<br>228/8 |
| 4,331,280 A | * | 5/1982 | Terabayashi .......... | B23K 20/12<br>228/114.5 |
| 4,521,237 A | | 6/1985 | Logothetis | |
| 4,523,968 A | | 6/1985 | McCool | |
| 4,661,300 A | | 4/1987 | Daugherty | |
| 4,998,663 A | * | 3/1991 | Cakmak ................ | B23K 20/12<br>228/103 |
| 5,599,325 A | | 2/1997 | Ju et al. | |
| 5,697,545 A | * | 12/1997 | Jennings ............... | B23K 20/10<br>228/112.1 |
| 5,846,513 A | | 12/1998 | Carroll et al. | |
| 6,030,371 A | * | 2/2000 | Pursley ............. | A61M 25/0009<br>427/195 |
| 6,103,037 A | | 8/2000 | Wilson | |
| 6,402,677 B1 | | 6/2002 | Jacobs | |
| 6,492,037 B2 | * | 12/2002 | Shindo ................... | B23K 20/22<br>428/615 |
| 6,740,277 B2 | | 5/2004 | Howell et al. | |
| 8,465,469 B2 | | 6/2013 | Brightbill | |
| 10,272,520 B2 | * | 4/2019 | Schmicker ............. | B23K 20/12 |
| 2011/0139754 A1 | * | 6/2011 | Romanowski .... | A61M 25/0014<br>219/121.64 |
| 2012/0010511 A1 | * | 1/2012 | O'Laughlin ............. | A61B 8/12<br>600/461 |
| 2015/0336203 A1 | * | 11/2015 | Zhai ........................ | B29C 65/06<br>228/2.1 |

FOREIGN PATENT DOCUMENTS

| | | | | | |
|---|---|---|---|---|---|
| CN | 201848997 U | | 6/2011 | | |
| CN | 201948997 U | * | 8/2011 | | |
| JP | 3770814 | * | 2/2006 | ............. | B23K 31/00 |
| JP | 3770814 B2 | * | 4/2006 | | |

OTHER PUBLICATIONS

Extended European Search Report in corresponding EP Application No. 18847668.3, dated Apr. 7, 2021,8 pages.
Examination Report issued in corresponding India Application No. 202017008886, dated May 17, 2022,6 pages.
Office Action in corresponding Canadian Patent Application No. 3,073,526, dated Dec. 12, 2024, 4 pages.
EPO Communication pursuant to Article 94(3) EPC in corresponding EP Application No. 18 847 668.3, dated Jun. 21, 2023, 6 pages.
India Patent Office Hearing Notice in corresponding India Application No. 202017008886, dated Jun. 25, 2025, 2 pages.

* cited by examiner

ROTATION DIRECTION
OF ROTATION MEMBER

CARRIAGE MOVEMENT
DIRECTION

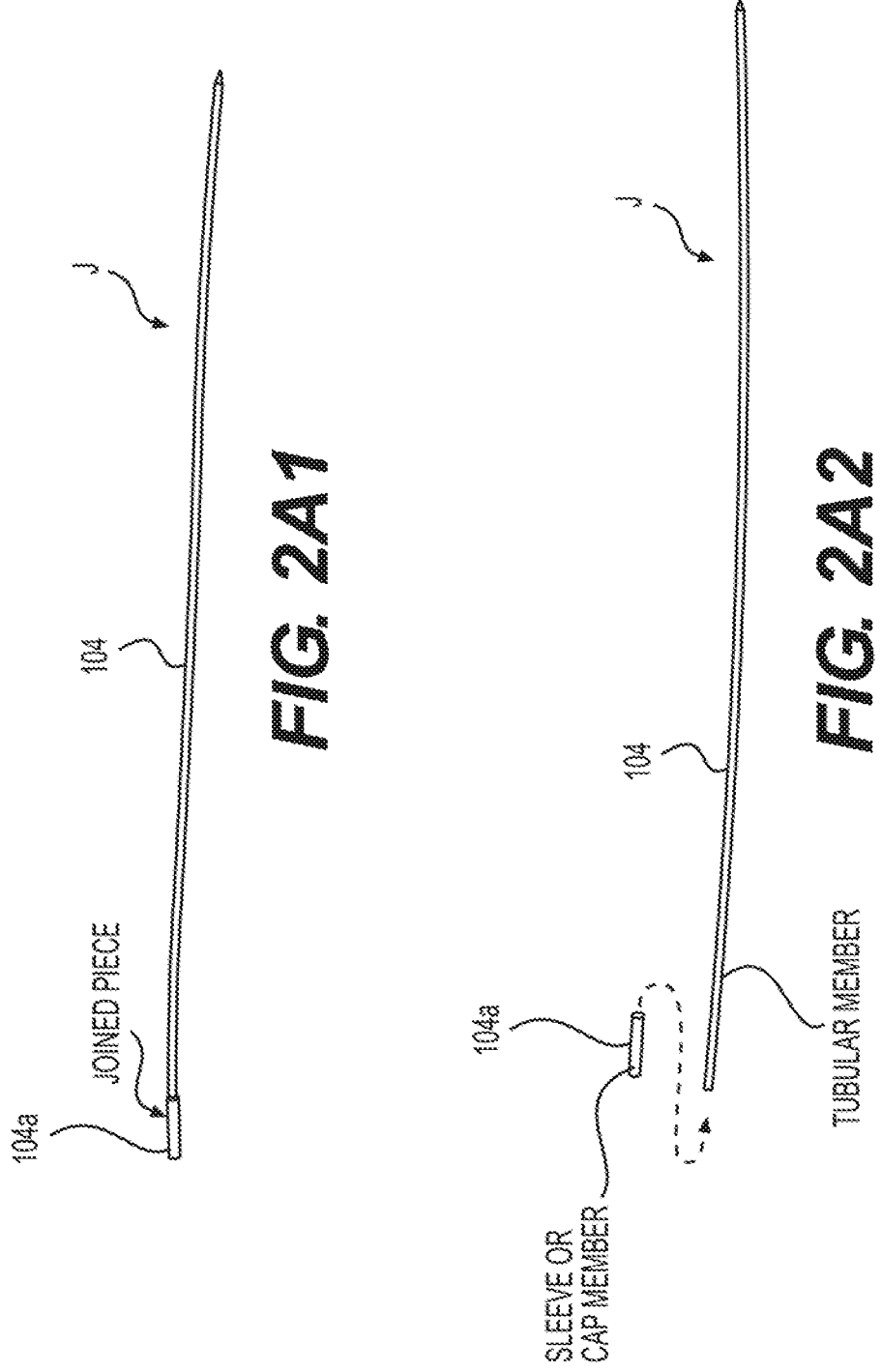
104
104a
JOINED PIECE
*FIG. 2A1*
104
104a
SLEEVE OR
CAP MEMBER
TUBULAR MEMBER
*FIG. 2A2*

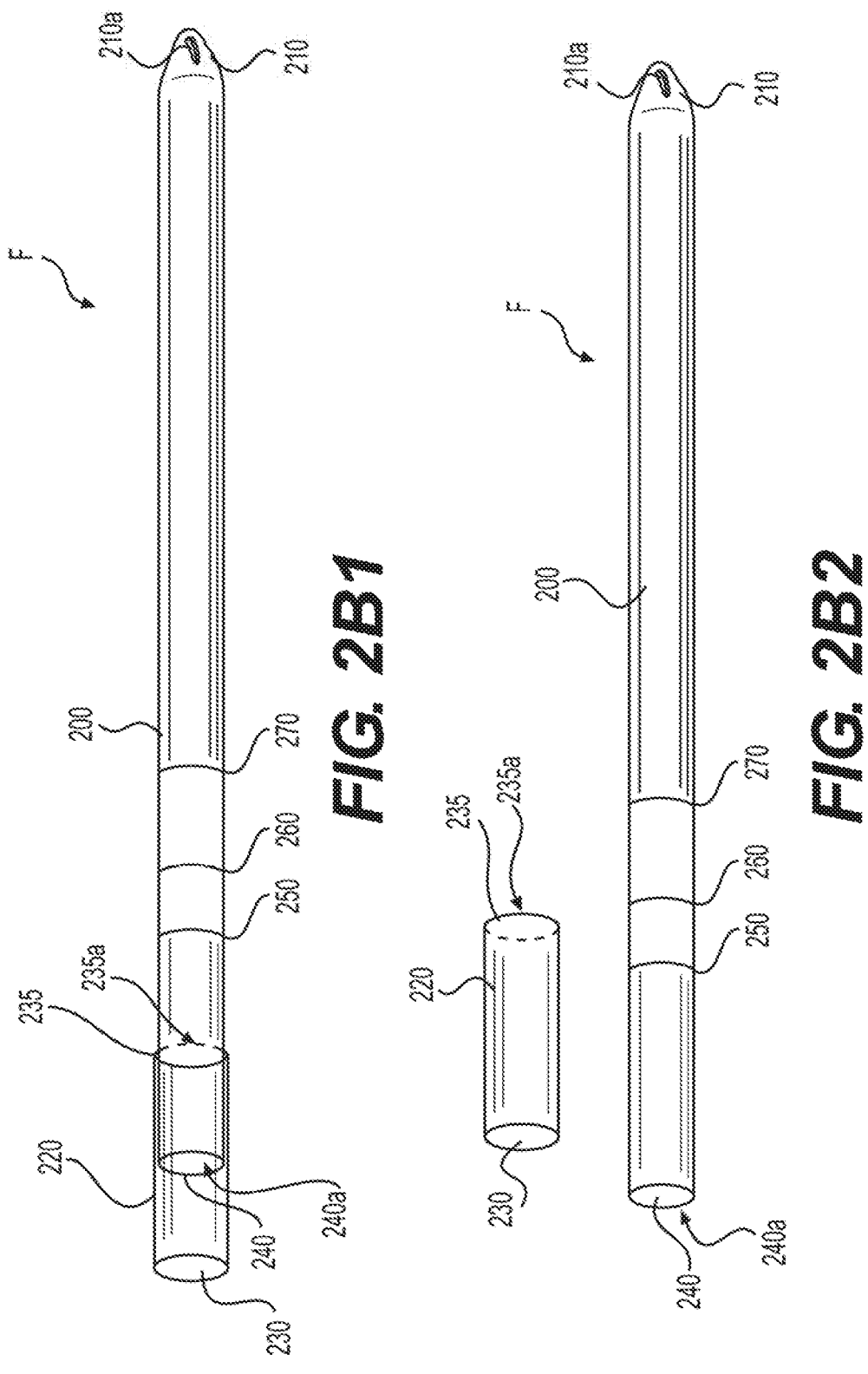
*FIG. 2B1*
*FIG. 2B2*

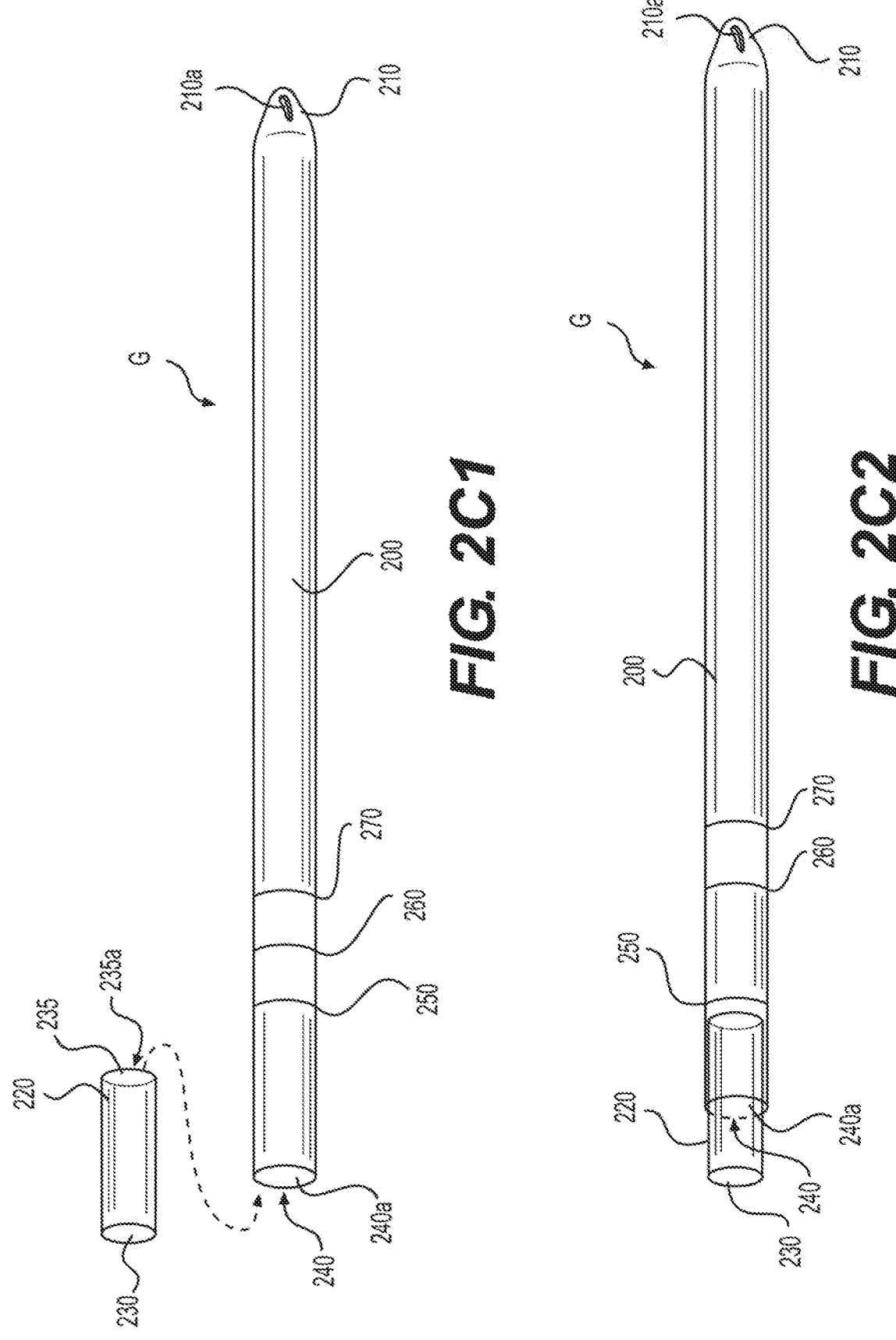
*FIG. 2C1*
*FIG. 2C2*

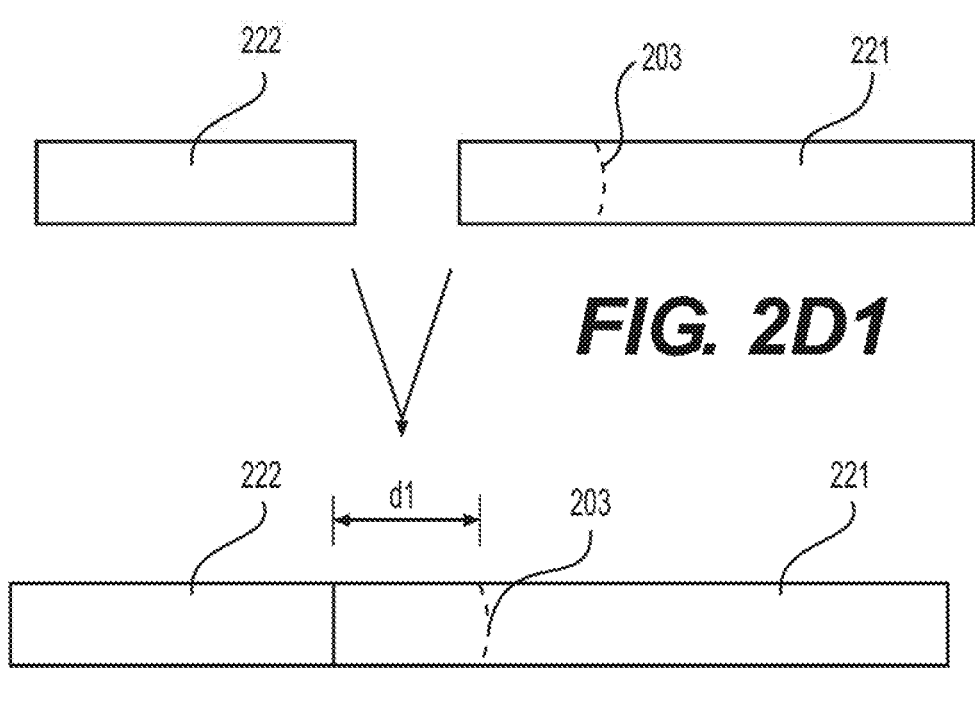
FIG. 2D1
FIG. 2D2
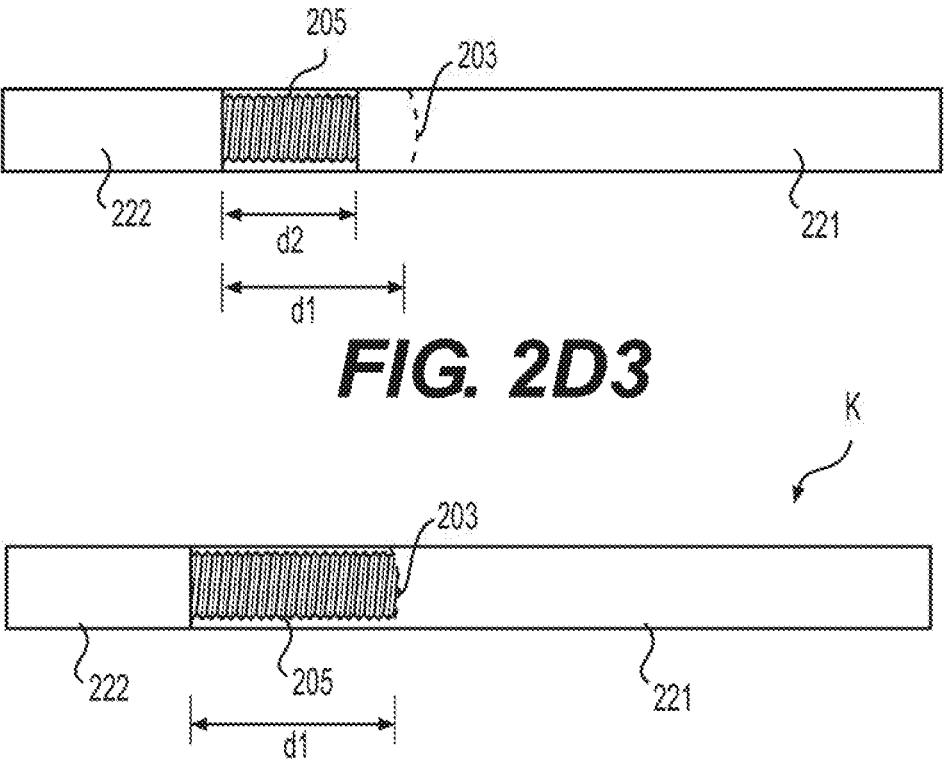
FIG. 2D3
FIG. 2D4

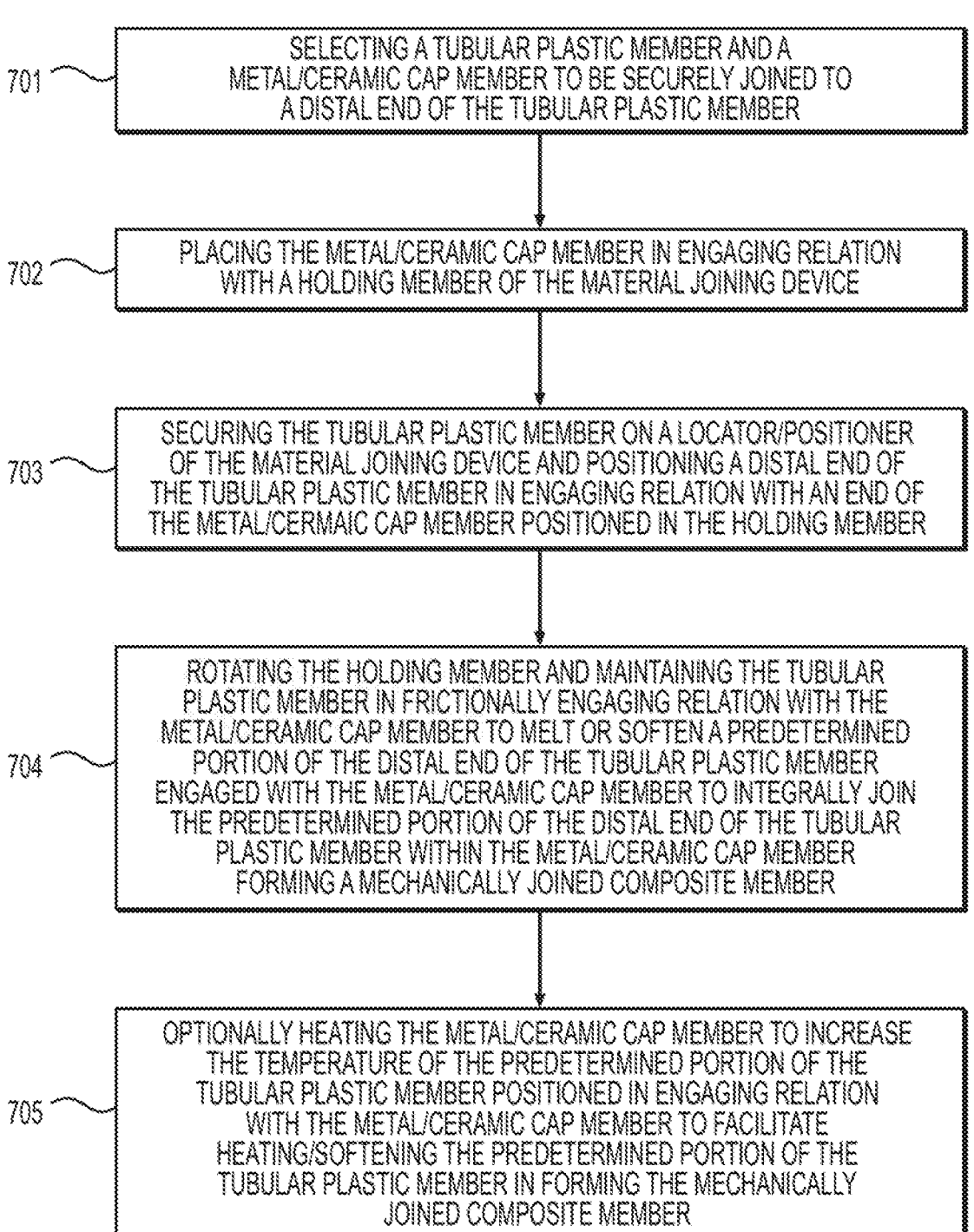

700

701 — SELECTING A TUBULAR PLASTIC MEMBER AND A METAL/CERAMIC CAP MEMBER TO BE SECURELY JOINED TO A DISTAL END OF THE TUBULAR PLASTIC MEMBER

702 — PLACING THE METAL/CERAMIC CAP MEMBER IN ENGAGING RELATION WITH A HOLDING MEMBER OF THE MATERIAL JOINING DEVICE

703 — SECURING THE TUBULAR PLASTIC MEMBER ON A LOCATOR/POSITIONER OF THE MATERIAL JOINING DEVICE AND POSITIONING A DISTAL END OF THE TUBULAR PLASTIC MEMBER IN ENGAGING RELATION WITH AN END OF THE METAL/CERMAIC CAP MEMBER POSITIONED IN THE HOLDING MEMBER

704 — ROTATING THE HOLDING MEMBER AND MAINTAINING THE TUBULAR PLASTIC MEMBER IN FRICTIONALLY ENGAGING RELATION WITH THE METAL/CERAMIC CAP MEMBER TO MELT OR SOFTEN A PREDETERMINED PORTION OF THE DISTAL END OF THE TUBULAR PLASTIC MEMBER ENGAGED WITH THE METAL/CERAMIC CAP MEMBER TO INTEGRALLY JOIN THE PREDETERMINED PORTION OF THE DISTAL END OF THE TUBULAR PLASTIC MEMBER WITHIN THE METAL/CERAMIC CAP MEMBER FORMING A MECHANICALLY JOINED COMPOSITE MEMBER

705 — OPTIONALLY HEATING THE METAL/CERAMIC CAP MEMBER TO INCREASE THE TEMPERATURE OF THE PREDETERMINED PORTION OF THE TUBULAR PLASTIC MEMBER POSITIONED IN ENGAGING RELATION WITH THE METAL/CERAMIC CAP MEMBER TO FACILITATE HEATING/SOFTENING THE PREDETERMINED PORTION OF THE TUBULAR PLASTIC MEMBER IN FORMING THE MECHANICALLY JOINED COMPOSITE MEMBER

*FIG. 4A*

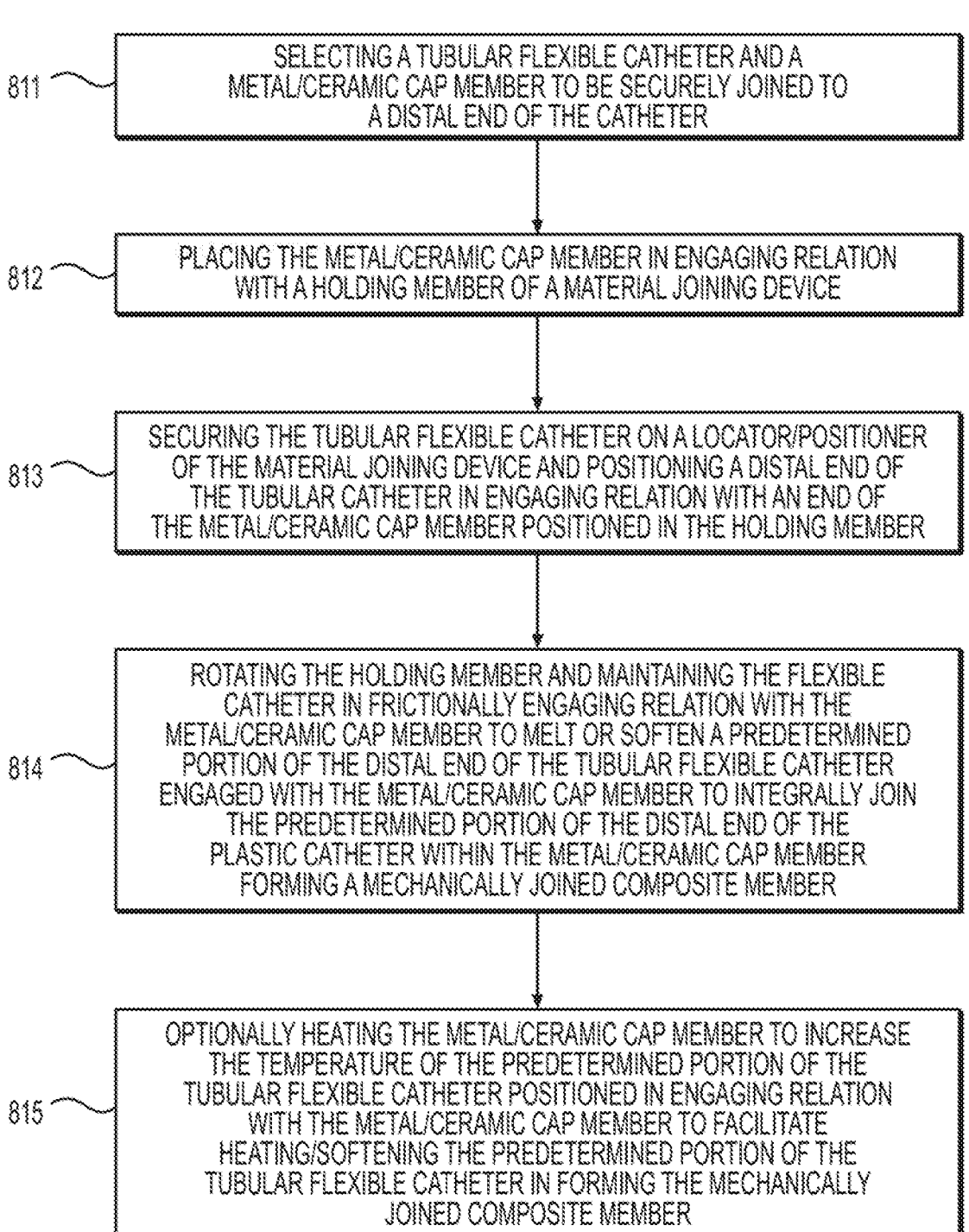

800

811 — SELECTING A TUBULAR FLEXIBLE CATHETER AND A METAL/CERAMIC CAP MEMBER TO BE SECURELY JOINED TO A DISTAL END OF THE CATHETER

812 — PLACING THE METAL/CERAMIC CAP MEMBER IN ENGAGING RELATION WITH A HOLDING MEMBER OF A MATERIAL JOINING DEVICE

813 — SECURING THE TUBULAR FLEXIBLE CATHETER ON A LOCATOR/POSITIONER OF THE MATERIAL JOINING DEVICE AND POSITIONING A DISTAL END OF THE TUBULAR CATHETER IN ENGAGING RELATION WITH AN END OF THE METAL/CERAMIC CAP MEMBER POSITIONED IN THE HOLDING MEMBER

814 — ROTATING THE HOLDING MEMBER AND MAINTAINING THE FLEXIBLE CATHETER IN FRICTIONALLY ENGAGING RELATION WITH THE METAL/CERAMIC CAP MEMBER TO MELT OR SOFTEN A PREDETERMINED PORTION OF THE DISTAL END OF THE TUBULAR FLEXIBLE CATHETER ENGAGED WITH THE METAL/CERAMIC CAP MEMBER TO INTEGRALLY JOIN THE PREDETERMINED PORTION OF THE DISTAL END OF THE PLASTIC CATHETER WITHIN THE METAL/CERAMIC CAP MEMBER FORMING A MECHANICALLY JOINED COMPOSITE MEMBER

815 — OPTIONALLY HEATING THE METAL/CERAMIC CAP MEMBER TO INCREASE THE TEMPERATURE OF THE PREDETERMINED PORTION OF THE TUBULAR FLEXIBLE CATHETER POSITIONED IN ENGAGING RELATION WITH THE METAL/CERAMIC CAP MEMBER TO FACILITATE HEATING/SOFTENING THE PREDETERMINED PORTION OF THE TUBULAR FLEXIBLE CATHETER IN FORMING THE MECHANICALLY JOINED COMPOSITE MEMBER

*FIG. 4B*

APPARATUS AND METHOD FOR JOINING METAL SLEEVE ONTO A TUBE

BACKGROUND OF THE INVENTION

1. Field of the Invention

The present invention relates generally to a method of making a catheter for medical purposes, and more particularly, to an apparatus and method for attaching a flexible tube catheter to a metal or ceramic sleeve or cap member to form a composite product.

2. Description of Related Art

Medical devices, such as catheters, have been developed for insertion into the tissues of a body cavity of a patient to introduce or remove fluids. A catheter includes a flexible tube with a distal end, which may be open or closed. The catheter is inserted into a body opening for draining fluids. In particular, the catheter may be a urinary catheter for insertion into a urinary pathway for collecting the fluids in this pathway. In the distal end region of the catheter, the tube is provided with at least one opening for collecting fluid and draining the body opening, in particular the urinary pathway.

In the past, various assortments of catheters, such as Foley catheters and endotracheal tubes including intravenous catheters (IV) have been proposed for use in patients. For example, U.S. Pat. No. 6,740,277 discloses a catheter for use with a needle having a tip and a method of forming a catheter by extruding a flexible, bio-compatible, thermoplastic material into a tube. In the case of urinary catheters, a conventional Foley catheter is normally constructed having a shaft defining a drainage lumen extending from a drainage eye adjacent a distal end of the shaft and an inflation lumen in a wall of the shaft, and having an expansible balloon overlying a distal portion of the shaft and defining a cavity communicating with the inflation lumen.

Also, it is well known to treat tumors with localized radiation by implanting radioactive seeds within the body of the patient within or in the vicinity of the tumor. The seeds typically comprise I-125, Pd-103, or other suitable radioactive agents contained within a pellet or seed to prevent migration of the radioactive material throughout the body of the patient. Such radioactive seeds, known as "brachytherapy" seeds, are conventionally implanted within the body of the patient by advancing the seeds through a hollow needle. The brachytherapy can include locations in prostate, breast, liver, head and neck, urethra, rectum, and other areas.

For example, U.S. Pat. No. 6,402,677 B1 to Jacobs, incorporated herein by reference in its entirety, discloses a needle for implanting radioactive seeds into the body of a patient, comprising a hollow cannula defining a lumen; and a push stylet telescopically receivable within said hollow cannula for advancing radioactive seeds through said lumen; said hollow cannula having a side wall and an opening formed in said side wall through which at least a portion of said lumen can be visualized.

Various methods have been suggested for preparing a catheter. For example, U.S. Pat. No. 6,103,037 discloses a method for manufacturing braid reinforced catheters with or without the axial weld joints. In the exemplary embodiment, the process relates to the manufacture of a catheter having inner and outer layers sandwiched about a braided tube layer. The inner layer is desirably formed from Teflon® while the outer layer is provided in the form of three axial jacket sections, one of which comprises nylon and the others of which comprise a polyether block amid (PEBA), such as that commercially available under the name Pebax®.

For example, U.S. Pat. No. 8,465,469 B2, incorporated herein by reference in its entirety, discloses a reinforced catheter having a non-filamentous, seamless metal tube interposed between a polymeric hollow core and a polymeric outer jacket. The metal tube may have a pattern of apertures through which the hollow core and the polymeric outer jacket are adhered to each other. The metal tube forms a reinforcement layer that can be thinner than is practically achievable by known filamentous reinforcements.

U.S. Pat. No. 5,599,325 incorporated herein by reference in its entirety, describes a catheter with reinforcing sleeve used for diagnostic intravascular diagnostics having an elongated tubular body with a proximal end, a distal end and a lumen extending therebetween where the tubular body is formed with an inner layer consisting essentially of an unmodified polyamide polymer, preferably Nylon-12.

Moreover, U.S. Pat. No. 5,846,513 incorporated herein by reference in its entirety, discloses a percutaneously insertable radiation detecting probe, an associated analyzer, and a percutaneously insertable tumor removing instrument. The system is arranged to be used with a tumor localizing radiopharmaceutical. The radiation detecting probe includes a needle unit having a radiation sensor component therein and a handle to which the needle unit is releasably mounted.

Also, for example, U.S. Pat. No. 4,661,300 discloses a method of tipping one end of an IV catheter, desirably a catheter made of a thermoplastic polyurethane, that includes mounting the catheter to be tipped onto a mandrel supported on a carriage. A die having an interior molding surface, with at least one portion of which is tapered according to the tip desired on the catheter, is aligned axially with the mandrel. The carriage is moved along a guide means toward the die such that the end of the catheter to be tipped engages the interior molding surface. The carriage is halted at a point after the catheter has engaged the tapered portions of the interior molding surface of the die, and is biased toward the die with only sufficient force to cause the catheter to move further into the die as the catheter is heated by RF energy.

Typical catheters or flexi needle devices, for example, incorporating metal joints on or with the plastic tube portions may not be completely satisfactory, such as in relation to the desired length or bond strength of the joined members. Therefore, it is desirable to improve upon prior catheter and flexi needle constructions by providing a method, apparatus and product that incorporates a metallic or ceramic end piece or member into or with the flexible catheter or tubular member without the use or addition of a synthetic or natural adhesive or other joining material in forming the bond to join the metal or ceramic member to or with the flexible tubular member. This method of attaching the metal or ceramic piece not only increases the retention of the metal or ceramic piece during internal use but promotes creating a more desirable, efficient and cost effective commercial production of the joined product, for example.

Thus, a flexi needle fixture device to attach a metal or ceramic sleeve/tip at the distal end of a tubular member, such as a catheter or in forming a flexi needle, addressing the aforementioned needs is desired.

SUMMARY OF THE INVENTION

Embodiments of methods and apparatuses include, but are not limited to, embodiments of a radiation probe used in the detection of radiation from cancer treatment and quantitating the radiation from an area of interest in a body or organism, such as a human, animal or reptilian body or other organism, are described, such as for human, veterinary or other biological diagnoses and treatments. In an embodiment, a method of preparing a catheter or a flexi needle includes the steps of: a) selecting a tubular member, such as a tubular biocompatible plastic member, and a metal or ceramic sleeve or cap member to be securely joined to a distal end of the tubular member; b) mounting the metal or ceramic sleeve or cap member in engaging relation onto a mandrel piece of a material joining device; c) securing the tubular member, such as a tubular biocompatible plastic member, on a locator/positioner or positioning member associated with a carriage of the material joining device; d) positioning the tubular member in coaxial relation with the metal or ceramic sleeve or cap member positioned on the mandrel piece; e) moving the carriage towards the mandrel piece such that a distal end of the tubular member, such as the tubular biocompatible plastic member, engages with an open hollow end of the metal or ceramic cap member positioned in the mandrel piece or an open hollow end of the tubular member engages with the end of the metal or ceramic sleeve or cap member positioned in the mandrel piece; and f) rotating the mandrel piece and maintaining the tubular member, such as a tubular biocompatible plastic member, in frictionally engaging relation with the metal or ceramic sleeve or cap member to melt or soften a predetermined portion of the distal end of the tubular member, such as a tubular biocompatible plastic member, engaged with the metal or ceramic sleeve or cap member to integrally join the tubular member to the metal or ceramic sleeve or cap member.

In another embodiment, in the method of preparing a tubular member capped with a metal piece the tubular member is a flexible plastic catheter. Also, the methods and apparatuses described herein include embodiments of methods and apparatuses for joining a first member having a first glass transition temperature, a first melting point or a first softening point to a second member having a second glass transition temperature, a second melting point, or a second softening point, the second glass transition temperature, the second melting point or the second softening point being lower that the first glass transition temperature, the second melting point or the second softening point, respectively, and embodiments of the integrally formed joined member including the first member and the second member. Thus, various suitable materials, other than those disclosed herein, such as piping or conduit materials for various industrial, plumbing, or other applications, can be joined together to provide integrally formed products using methods and apparatuses of embodiments of the present invention to provide formed products in accordance with the described embodiments herein, and, as such, the various applications, products, methods and apparatuses to which the disclosure applies should not be construed in a limiting sense.

In another embodiment, a device for joining a tubular metal or ceramic sleeve or cap member onto or with a tubular member includes a) a base comprising a bearing block support member comprising a shaft assembly having a rotatable member associated with a mandrel piece or a holding member, rotatable around a linear axis of the shaft assembly; b) the mandrel piece or holding member having an end portion shaped to form a holder, such as a hollow cylinder, adapted to hold or support the ceramic sleeve or cap member, as can be of a generally tubular or other suitable shape, to be fitted onto or joined with the tubular member; c) a locator or positioning member positioned over or in association with a movable carriage on the base configured to position and hold a tubular member to be inserted and fitted onto the metal or ceramic sleeve or cap member; d) a rotation driver including a first motor or a manual rotation member operatively coupled to the shaft assembly configured to rotate the mandrel piece around a linear axis of the shaft assembly; and e) a carriage driver including a second motor or a manual driver member operatively coupled with the carriage to drive the carriage towards the mandrel piece or holding member holding the metal or ceramic sleeve or cap member to join the metal or ceramic sleeve or cap member onto or with the tubular member.

These and other features of the present invention will become readily apparent upon further review of the following specification and drawings.

DESCRIPTION OF THE DRAWINGS

FIG. 2A1 shows an embodiment of the metal or ceramic sleeve or cap member individually and as integrally joined to the tubular member, such as a biocompatible plastic member, according to the present invention.

FIG. 2A2 shows an embodiment of a metal or ceramic sleeve or cap member and a tubular member, such as a biocompatible plastic member, individually, according to the present invention.

FIG. 2B1 shows the cross-sectional view of an embodiment of a flexi needle having the metal or ceramic tip or cap member being joined with the tubular body.

FIG. 2B2 shows a perspective view of an embodiment of the metal or ceramic tip or cap member in relation to and as being integrally joined with or incorporated into the tubular member in an embodiment of a flexi needle, according to the present invention.

FIG. 2C1 shows the cross-sectional view of an embodiment of a flexi needle having the metal or ceramic tip or cap member being integrally joined with the tubular member and also includes position markers to indicate a corresponding predetermined length of the tubular member when joined with the metal or ceramic tip or cap member to facilitate the joining process or to facilitate positioning or locating the flexi needle when used for a treatment or application, according to the present invention.

FIG. 2C2 shows a perspective view of an embodiment of individual components of the flexi needle of FIG. 2C1 including the metal or ceramic tip or cap member and the tubular member, with the position markers on the tubular member, according to the present invention.

FIG. 2D1, FIG. 2D2, FIG. 2D3 and FIG. 2D4 show an embodiment of a process of joining the metal or ceramic tip or cap member with a tubular member, such as a catheter tube, according to the present invention.

FIG. 3 shows a block diagram of an embodiment of an automated or mechanized material joining device, apparatus or system, such as a flexi needle fixture device or apparatus with various components thereof in joining the metal or ceramic tip or cap member with the tubular member, according to the present invention.

FIG. 4A shows a process flow block diagram illustrating an embodiment of a method for preparing and joining a first member of a first material to a second member of a second material, such as joining a metal or ceramic tip or cap member with a tubular member, according to the present invention.

FIG. 4B shows a process flow block diagram illustrating an embodiment of a method for preparing and joining a first member of a first material and a second member of a second material, such as joining a flexible plastic catheter fitted with the metal or ceramic cap member, according to the present invention.

Unless otherwise indicated, similar reference characters denote corresponding features consistently throughout the attached drawings.

DETAILED DESCRIPTION

Figure 1A:
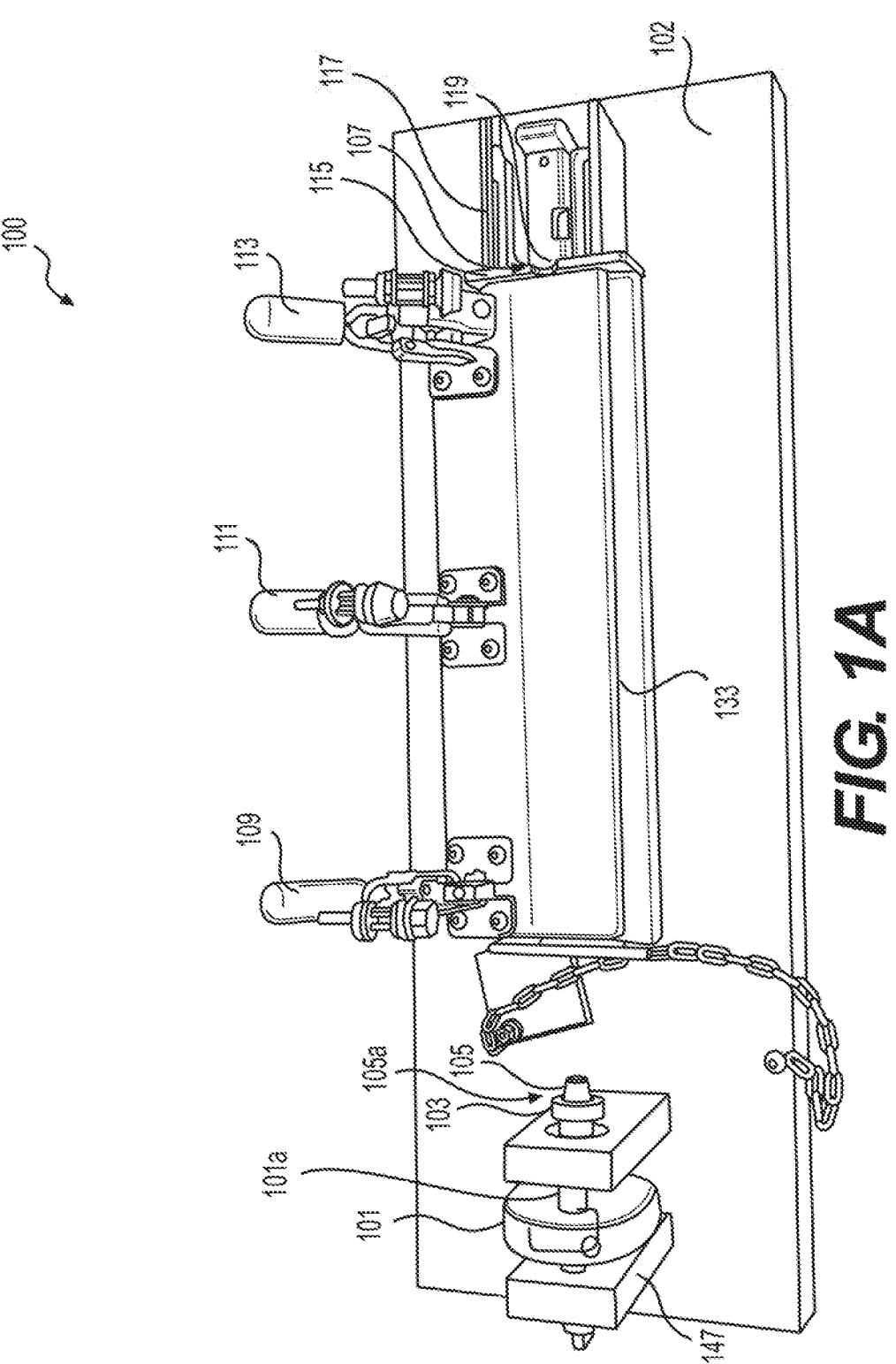
FIG. 1A is a perspective view illustrating an embodiment of a material joining device, such as a flexi needle fixture device, for attaching the metal or ceramic tip or cap member to the tubular member, such as a catheter, according to the present invention.

Described herein are various exemplary embodiments of flexi needle fixture apparatuses and methods for joining a metal or ceramic sleeve or cap member at the distal end of a tubular member and resultant products, such as a plastic catheter, such as for a flexi needle or other catheter, delivery or positioning or location device, for example.

The exemplary embodiments of a metal catheter composites have both internal (in vivo) and external (ex-vivo) use near the vicinity of the target tissue particularly breast and prostate of a patient. Embodiments of catheters and flexi needles have applicability not only to humans, but to animals and reptiles or other biological applications, as well, for example. Also, embodiments of apparatuses and methods for joining a metal or ceramic sleeve or cap member to a tubular member, or for joining first and second members, such as of first and second materials having different glass transition temperatures or different melting points, can also have other industrial or non-biological applications, such as for piping applications, for example.

In an embodiment, a method for preparing a catheter or a flexi needle includes the steps of: a) selecting a tubular member, such as a tubular biocompatible plastic member, and a metal or ceramic sleeve or cap member to be securely joined to a distal end of the tubular member; b) mounting the metal or ceramic sleeve or cap member in engaging relation onto a holding member mandrel piece of a material joining device; c) securing the tubular biocompatible plastic member on a locator/positioner or positioning member positioned on a carriage of the material joining device; d) positioning the tubular member on the locator/positioner or positioning member on the carriage of the material joining device in coaxial or opposing relation with the mandrel piece or holding member and the metal or ceramic sleeve or cap member; e) moving the carriage towards the mandrel piece such that a distal end of the tubular plastic member engages with an open hollow end of or engages with an end of the metal or ceramic sleeve or cap member positioned in the mandrel piece or holding member; and f) rotating the mandrel piece or holding member and maintaining the tubular plastic member in frictionally engaging relation with the metal or ceramic sleeve or cap member to melt or soften a predetermined portion of the distal end of the tubular plastic member engaged with the metal/ceramic sleeve member to integrally join the metal or ceramic sleeve or cap member with the tubular member.

In another embodiment, the tubular biocompatible plastic member can be engaged with the metal or ceramic sleeve or cap member either over or under the metal or ceramic sleeve or cap member, for example.

In the method of preparing a tubular member capped with a metal/ceramic piece the tubular member is a flexible plastic catheter. The mandrel piece typically is part of a holding member, such as can include a vise, to hold and grip the metal or ceramic piece for the joining process.

In various embodiments, the metal for the metal sleeve can be selected from the group consisting of steel, tungsten, tin, copper, bronze, gold platinum, silver and alloy thereof, for example.

Also, in embodiments, the inside surface of the metal or ceramic sleeve or cap member is smooth or corrugated to enhance retention and engagement with the tubular member, such as a tubular plastic member, for example.

In various embodiments, the outer diameter of the tubular plastic member is in the range of from about 1 mm to about 5 cm and the length of the tubular member is between about 1 cm to about 100 cm, for example, as can depend on the use or application, and should not be construed in a limiting sense. Also, in various embodiments, the outer diameter of the metal or ceramic sleeve or cap member is in the range of from about 1 mm to about 5 cm and the length of the metal or ceramic sleeve or cap member is between about 1 cm to 10 cm, for example, as can depend on the use or application, and should not be construed in a limiting sense.

Typically, the flexible biocompatible plastic catheter as a tubular member is made of a polymeric material, wherein the polymeric material is selected from the group consisting of polyurethane, polyethylene, polymethyl methacrylate (PMMA), polycarbonate, styrenic block copolymers, polybutylene terephthalate (PBT), Teflon, Nylon, and poly vinyl chloride (PVC), for example, as can depend on the use or application, and should not be construed in a limiting sense.

In various embodiments, in the method of preparing a tubular member capped with a metal piece the tubular member can include position markers to facilitate precisely fitting of a predetermined length of the tubular member with the metal or ceramic sleeve or cap member. Also, such position markers can be used to facilitate placement, positioning or location of the joined product, for example.

In another embodiment, the method of preparing a tubular member capped with a metal or ceramic piece or cap member can further include heating the mandrel piece to increase a temperature of a predetermined portion of the tubular biocompatible plastic member or the tubular member positioned in engaging relation with the metal or ceramic cap to melt or soften the tubular member to facilitate the joining and retention of the metal or ceramic piece or cap member with the tubular member.

In embodiments of the method for preparing a tubular member capped with a metal or ceramic sleeve or cap member, the step of rotating the mandrel piece can be conducted manually or by automation. Desirably, the rotating step is conducted manually by visually comparing the length of the tubular member as it engages with and is joined to the metal or ceramic sleeve or cap member.

In another embodiment, the method for preparing a tubular member capped with a metal or ceramic sleeve or cap member can further include releasing the metal or ceramic sleeve or cap member from the mandrel device and reversing the carriage of the material joining device such that the tubular member integrally joined with the metal or ceramic piece as a formed joined product is removed from engagement with the mandrel device and the formed joined product is then removed from engaging relation with the locator/positioner or positioning member positioned on or associated with the carriage of the material joining device.

In another embodiment, the formed flexible biocompatible plastic catheter having the metal or ceramic tip or cap member is a needle for implanting brachytherapy radioactive seeds into the body of a patient, such as a human patient or an animal patient, for example.

In another embodiment, a device for joining a tubular metal or ceramic sleeve onto or with a tubular member is disclosed. The device includes a base comprising a bearing block comprising a shaft assembly having a rotatable member and a mandrel piece or holding member rotatable around a linear axis of the shaft assembly; b) the mandrel piece or holding member having an end portion shaped to form a holder, such as a hollow cylinder, adapted to hold or support the tubular metal or ceramic sleeve or cap member to be fitted onto or joined with the tubular member; c) a locator/positioner or positioning member positioned over or in association with a movable carriage located on or in association with the base configured to hold a tubular member to be inserted and fitted onto or with the metal or ceramic sleeve or cap member, as can be of a generally tubular shape or configuration; d) a rotation driver including a first motor or a manual rotation member operatively coupled to the shaft assembly configured to rotate the mandrel piece around a linear axis of the shaft assembly; and e) a carriage driver including a second motor or a manual driver member operatively coupled with the carriage to drive the carriage towards the mandrel piece holding the tubular metal or ceramic sleeve or cap member to join the tubular metal or ceramic sleeve or cap member on to the tubular member.

In another embodiment, the device for joining a metal or ceramic sleeve or cap member on to a tubular member further includes a drawer slide for sliding the carriage forward or rearward from the mandrel piece or holding member.

In another embodiment, the device for joining a metal or ceramic sleeve or cap member onto or with a tubular member can further include a heater, such as a heater collar member, positioned in surrounding relation to the mandrel piece or holding member to heat the mandrel piece or holding member holding the metal or ceramic sleeve or cap member to transfer heat to a portion of the tubular member in engaging relation with the ceramic sleeve or cap member to soften the portion of the tubular member in engaging relation with the ceramic sleeve or cap member to the softening point, melting point or glass transition temperature of the material forming the tubular member.

In another embodiment, the material joining device for joining a metal or ceramic sleeve or cap member onto or with a tubular member can further include a movement sensor to sense a moved distance or a change in position of the tubular member positioned on the carriage as can be operatively associated with a motor and/or a controller of the material joining device for driving the carriage to sense a moved distance of the tubular member, such as a catheter, to control a length of the tubular member to be joined to the metal or ceramic sleeve or cap member or a length of the tubular member in the formed product.

In another embodiment, the device for joining a metal or ceramic sleeve or cap member onto or with a tubular member can further include a controller/processor for controlling the movement of the distance of the carriage to selectively control a length of the tubular member joined to the metal or ceramic sleeve or cap member and/or to selectively control a rotational speed of the rotatable member associated with the mandrel piece or holding member to selectively control heating of the material forming the tubular member to facilitate the integral joining of the tubular member, such as controlling heat generated by a heater or by frictional engagement of the metal or ceramic sleeve or cap member with the tubular member.

In another embodiment, the material joining device for joining a metal or ceramic sleeve or cap member onto a tubular member further comprises a measurement device to determine a moved distance of the tubular member in a direction towards or away from the metal or ceramic sleeve or cap member.

In another embodiment, the material joining device for joining a metal or ceramic sleeve or cap member onto or with a tubular member can further include a power supply for providing power to various components of the material joining device, such as a controller/processor, a user interface, a display, motor(s), sensor(s), and heater(s), for example.

In another embodiment, the material joining device for joining a metal or ceramic sleeve or cap member onto or with a tubular member can further include a user interface display operatively associated with the controller/processor, for example.

As defined herein, the glass transient temperature (Tg) is one of the most important properties of any polymer and is the temperature region where a polymer transitions from a hard, glassy material to a soft, rubbery material. Also, the melting point of a material is the temperature or temperature range where a material changes from a solid state to a liquid state. The softening point of a material is the temperature or range of temperatures at which a material softens or begins to soften. The softening point can be determined, for example, by various suitable methods, as known in the art, such as by the Vicat method (ASTM-D1525 or ISO 306), Heat Deflection Test (ASTM-D648) or a ring and ball method (ISO 4625 or ASTM E28-67/E28-99 or ASTM D36 or ASTM D6493-11), The following described embodiments and examples are provided by way of illustration to further illustrate and describe exemplary flexi-needle assembly apparatuses and material joining devices and to illustrate and describe embodiments of methods of manufacturing flexi-needle apparatuses other catheter or industrial products formed by joining first and second materials having different glass transition temperatures, melting points or softening points, such as can be used in manufacturing a catheter having a tightly fitted ceramic or metal or cap member, and, as such, the description is not intended to limit the scope and application of the disclosure and, therefore, should not be construed in a limiting sense.

Figure 1B:
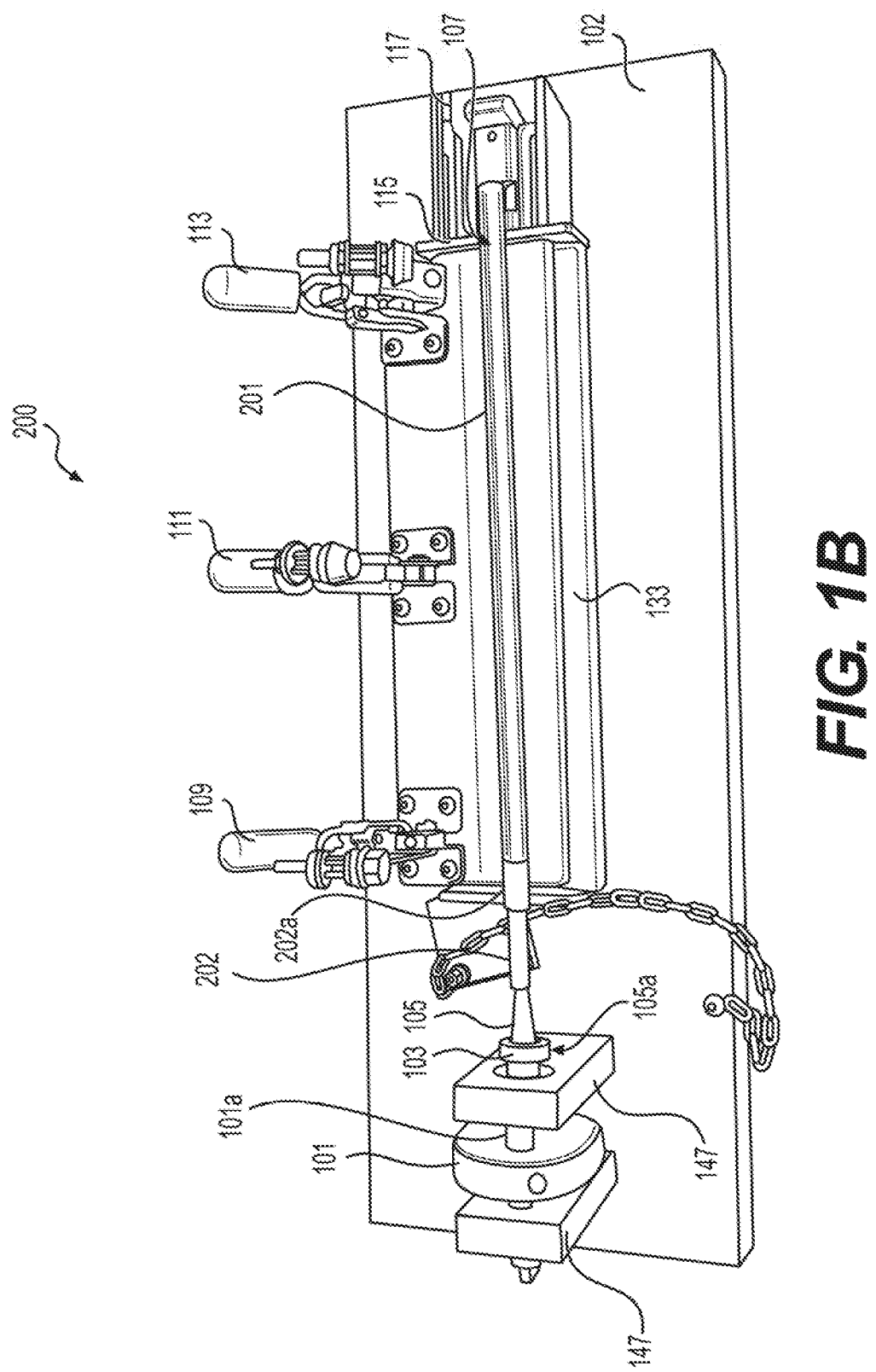
FIG. 1B a perspective view illustrating an embodiment of the material joining device, such as the flexi needle fixture device, of FIG. 1A having a catheter plastic tube placed along the longitudinal axis of the machine and a metal tip piece being held in the mandrel piece, according to the present invention.

Referring now to the figures, FIG. 1A shows the top perspective view of the apparatus or material joining device 100 for preparing the flexi needle product, such as illustrated in FIGS. 2A1-2C2, for example, and FIG. 1B shows the top perspective view of an apparatus 200, similar to the material joining device 100, and having a catheter plastic tube 201 placed along the longitudinal axis of the positioner or positioning member 107 and a metal or ceramic tip piece 202 being held in a mandrel, vise or holding member 105*a*, illustrating an embodiment positioning the metal or ceramic tip sleeve or cap member 202 into an open end 202*a* of the catheter plastic tube 201 to form the joined product, according to the present invention.

Figure 1C:
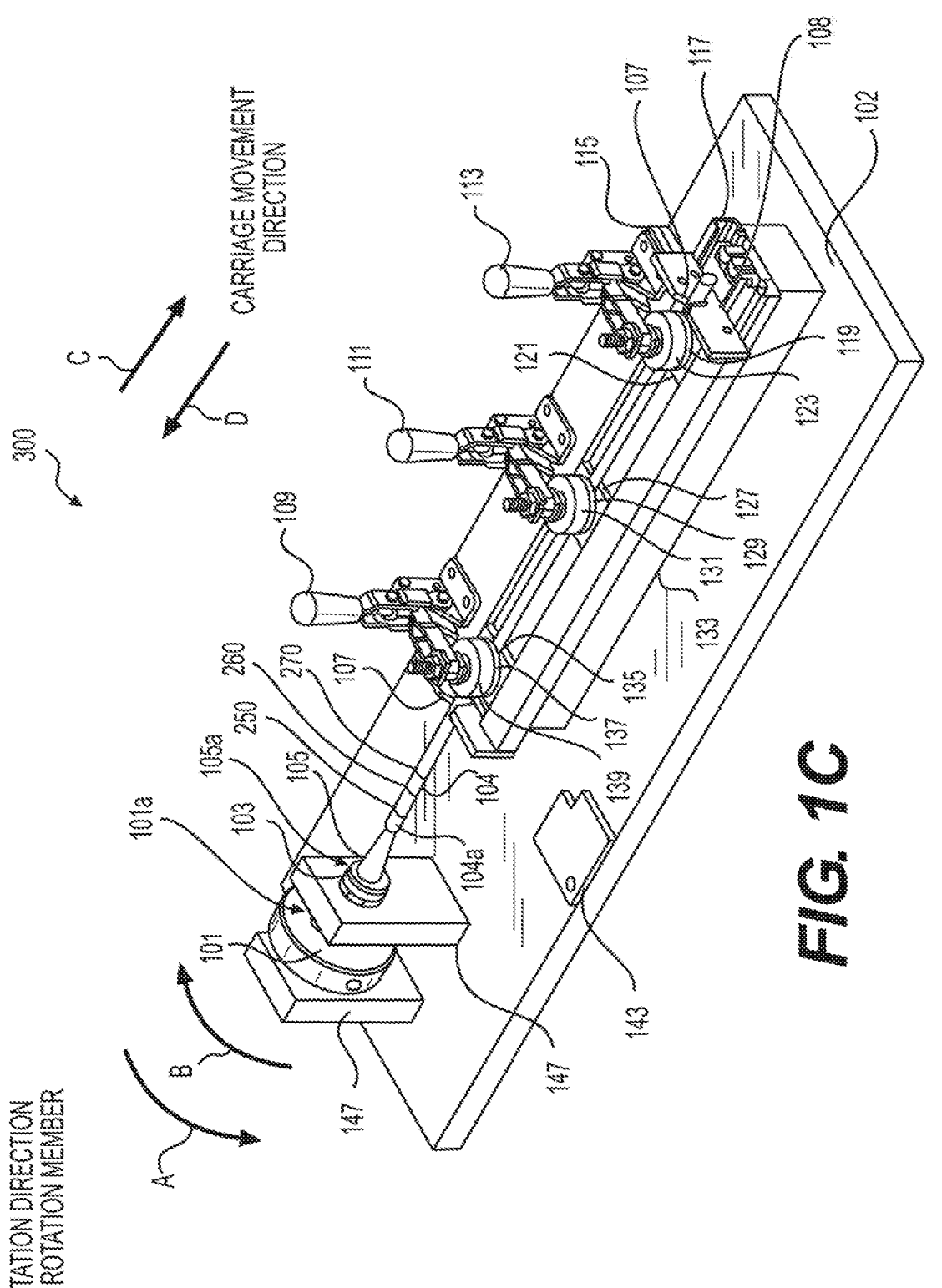
FIG. 1C a perspective view illustrating an embodiment of the material joining device, such as the flexi needle fixture device, of FIG. 1A, showing the various components of the device, according to the present invention.

Referring to FIGS. 1A, 1B and 1C, FIG. 1C provides a perspective view illustrating an embodiment of a flexi needle fixture device or a material joining device 300, similar to the material joining device 100 of FIG. 1A, showing the various components of the device 300 according to the present invention. The exemplary flexi-needle fixture assembly apparatus 300, similar to the material joining device 100, includes a base 102 having a setting or tube depth gauge 143 to measure a tubes dimension, such as a tube diameter, to facilitate positioning and aligning the first and second materials for the joining process, a bearing block 147 holding and supporting a holding member 105*a* including a suitable metallic or polymeric collar member 103, such as a metallic or a polyvinyl (PV) collar member, and a pin vise 105 (mandrel piece) coupled to a rotary grip or rotation member 101 communicating with and positioned along a shaft assembly 101*a*. The arrows A and B indicate respective rotation directions of the rotation member 101 in the joining process. The FIG. 1C device 300 also illustrates a slide mount 133 having a movable carriage 115 sliding over a drawer slide 117, having toggle clamps 111, 113 and 109 with clamp pucks 139, 131 and 123 resting on silicone pads 137, 129 and 119 attached over a corresponding another silicone pad 135, 127 and 121, respectively, to hold and position a tubular member, such as a tubular member 104 along a locator or positioning member 107 to be joined and attached with a metal or ceramic sleeve or cap member 104*a* clamped or positioned onto a mandrel piece or pin vise 105 of the holding member 105*a*. In various embodiments the metal or ceramic sleeve or cap member 104*a* and tubular member 104 can be any of various suitable materials, as can depend on the use and application and should not be construed in a limiting sense. For example, the metal or ceramic sleeve or cap member 104*a* can be a sleeve or cap member 104*a* of a suitable first material having a first melting point, a first softening point or a first glass transition temperature, and the tubular member 104 can be a tubular member 104 of a suitable second material having a second melting point, a second softening point or a second glass transition temperature, and the second melting point, the second softening point or the second glass transition temperature of the second material being less than the respective first melting point, the first softening point or the first glass transition temperature of the first material, for example.

Also, the arrows C and D indicate respective movement directions of the movable carriage 115 in the joining process.

Figure 1D:
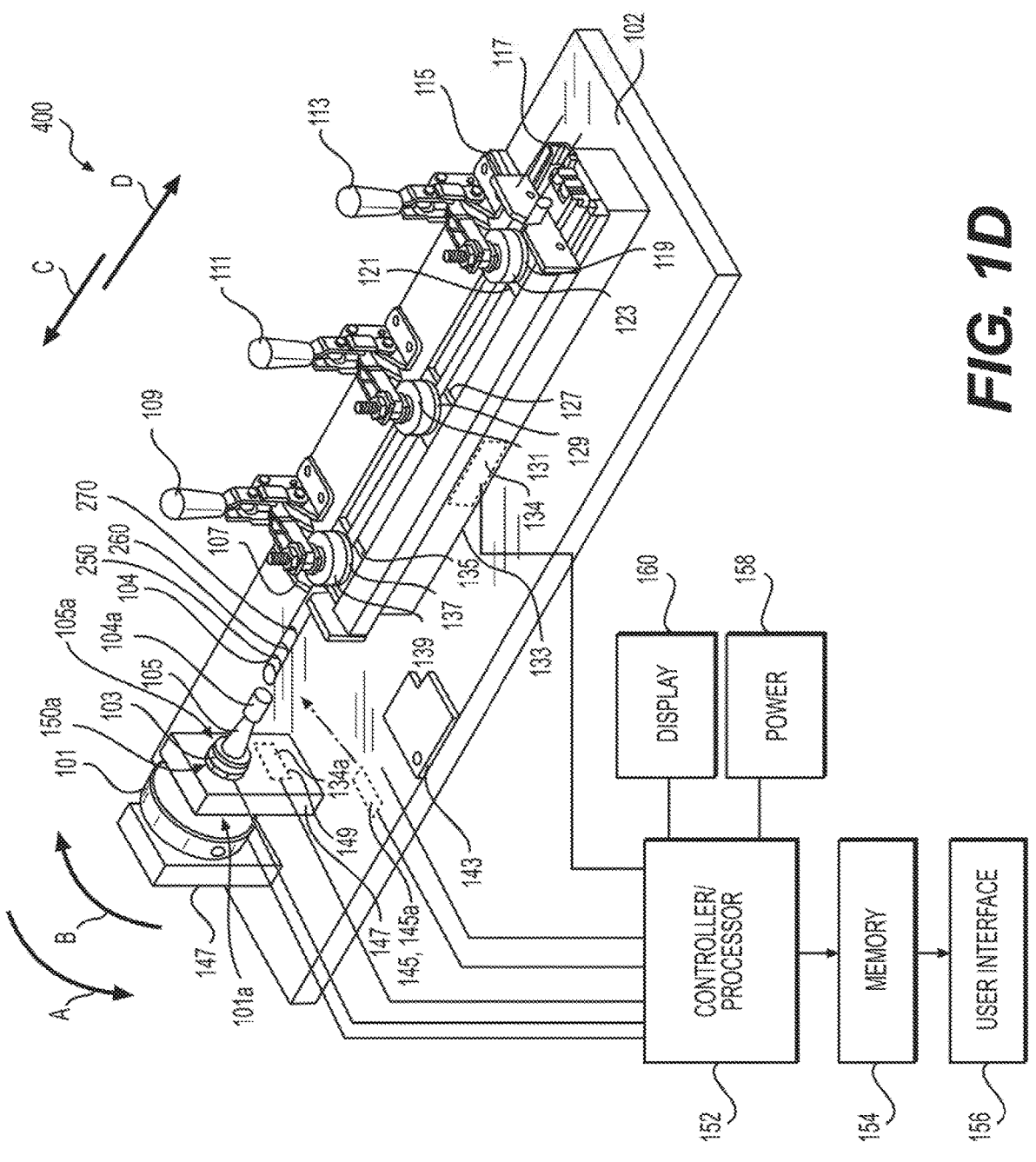
FIG. 1D a perspective view illustrating an embodiment of the material joining device, such as the flexi needle fixture device, of FIG. 1A, showing the various components including a controller processor/memory, a user interface and a display, according to the present invention.

FIG. 1D illustrates an exemplary material joining device or flexi-needle fixture assembly device 400, similar to the material joining device 100 of FIG. 1A, but provides an exemplary embodiment for automated or powered control of the joining process in forming the resultant product. The automated or powered material joining device 400 including a base 102 having a setting or tube depth gauge 143 to measure tube dimensions, such as a tube diameter, to facilitate positioning or aligning the first and second materials for the joining process, a bearing block 147 holding a collar member 103, such as a PV collar member, and pin vise 105 (mandrel piece) forming a holding member 105*a* coupled to a rotary application knob or rotation member 101 along a shaft assembly 101*a*. A slide mount 133 having a movable carriage 115 associated with a positioning member 107 sliding over a drawer slide 117, having toggle clamps 111, 113 and 109 with clamp pucks 139, 131 and 123 resting on silicone pads 137, 129 and 119 attached over another corresponding silicone pad 135, 127 and 121, respectively, is adapted to hold and position a tubular member 104 along a locator or positioning member 107 to be joined and attached with a metal or ceramic sleeve or cap member 104*a* held by the holding member 105*a*.

In FIG. 1D, the arrows A and B indicate respective rotation directions of the rotation member 101, and the arrows C and D indicate respective movement directions of the moveable carriage 115. The device 400 is configured to be powered by an electric power source 158, such as a battery or main electric line, and includes a carriage driver including a manual driver member or a first motor drive assembly including a first motor 134 to drive the movable carriage 115 with the tubular member 104 towards the holding member 105*a* holding the metal or ceramic sleeve or cap member 104*a* for the joining process. Also, in embodiments of the material joining device herein described, the moveable carriage 115 can also be driven by other suitable mechanical devices, such as a manual driver member 108, in communication with or associated with the carriage 115 as can be manually operated, for example. Also, the moveable carriage 115 can also be manually moved by a user of the material joining device, such as by a user's hand with moveable carriage 115, with the movable carriage 115 constituting and/or including the manual driver member 108, for example.

The device 400 also includes a rotation driver including the manual rotation member 101 or a second motor drive assembly including a second motor 134*a* powered by the electric power source 158 to drive the rotation member 101 and the drive the shaft assembly 101*a* to rotate the holding member 105*a* holding the metal or ceramic sleeve or cap member 104*a* to generate heat by frictional engagement of the metal or ceramic sleeve or cap member 104*a* with the tubular member 104 to soften a portion of the tubular member 104 to facilitate fitting, retaining and joining of the metal or ceramic sleeve or cap member 104*a* with the tubular member 104. The flexi needle fixture device or material joining device 400 can include a suitable sensor 145 to sense the moved distance of the tubular member 104 or to sense a certain mark or marks, such as position markers 250, 260 or 270, on the tubular member 104 to indicate a predetermined length of the tubular member 104 to be joined with the metal or ceramic sleeve or cap member 104*a* or to correspond to a predetermined length of the resultant joined product or a predetermined length of the tubular member 104 when joined with the metal or ceramic sleeve or cap member 104*a*, for example. The apparatus or device 400 can also include a measurement device 145*a* for determining a moved distance of the tubular member 104 during the joining process. The measurement device 145*a*, as can be a ruler type device or a suitable optoelectronic device as can be part or in conjunction with the sensor 145, for example.

The apparatus or device 400 can also include a suitable heater collar member 150*a* surrounding at least a portion of the holding member 105*a* including one or more of the collar member 103 or the mandrel or pin vise 105 to transfer heat one or more of the collar member 103 and/or the mandrel or pin vise 105 holding the metal/ceramic cap to heat the tubular member to its softening point, melting point or glass transition temperature ($T_g$) thereby transferring heat through or to the metal or ceramic sleeve or cap member 104*a* as needed to melt or soften the tubular member 104 when engaged with the metal or ceramic sleeve or cap member 104*a* during the fitting or joining process.

In the material joining device 400, the first and second motors 134 and 134*a*, that respectively power movement of the rotation member 101, the shaft assembly 101*a* and power movement of the moveable carriage 115, and the heater 150*a* can be controlled by a suitable controller/processor 152 that can be programmable and/or and have firmware, hardware and software to control or monitor the joining process or operation of the material joining device, such as the material joining device 400. The controller/processor 152 is associated with a suitable memory 154 and is operatively coupled to a user interface 156, all of which can be powered by the power supply 158, such as through the controller/processor 152. The power supply 158 can include an ON/OFF switch, indicator or button to indicate or control the power-on and power-off. The controller/processor 152 is in communication with various processing units and components of the material joining device, such as the material joining device 400, that perform various functions in the process of joining a first material and a second material that respectively have different melting points, softening points or glass transition temperatures, such as the tubular member 104 and the metal or ceramic sleeve or cap member 104*a*, such control can include manufacturing process control, information processing and sensor information reception/transmission indicating the moved distance of the tubular member 104 in relation to the holding member 105*a* or in relation to one or more position markers 250, 260 and 270 as can be associated with the tubular member 104, for example. The controller/processor 152, as part of the material joining device or system, such as the device 400, includes various components for receiving, processing, displaying and transmitting information related to the joining process.

For example, the device 400 can include a display device 160 which can be in communication with the controller/processor 152, as can be a touch pad type display device that can display the above described distance or length information and can control and provide information on the joining process. The display device 160 can be a personal computer, tablet, or cell phone device, for example, or other suitable display. The flexi-needle fixture assembly 400 can include a remote controller to remotely control the joining process.

Also, the controller/processor 152 in the material joining device 400 can represent, for example, a stand-alone computer, computer terminal, portable computing device, networked computer or computer terminal, or networked portable device. Data may be entered into the controller/processor 152 by the user via any suitable type of user interface 156, and can be stored in computer readable memories, such as the memory 154, which may be any suitable type of computer readable and programmable memory. Calculations, processing and analysis are performed by the controller/processor 152 or other processors of system components of the material joining device 400, which can be any suitable type of computer processor, and can be displayed to the user on the display 160, which can be any suitable type of computer display, for example.

The controller/processor 152 and other processors of the system components of the material joining device 400 can be associated with, or incorporated into, any suitable type of computing device, for example, a personal computer or a programmable logic controller (PLC) or an application specific integrated circuit (ASIC). The controller/processor 152, the user interface 156, the memory 154, the display 160, the processor components and the various system components of the material joining device 400, and any associated computer readable media are in communication with one another by any suitable type of data bus or other wired or wireless communication, as is well known in the art.

Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used as, in conjunction with or in addition to the memory 154, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Figure 1E:
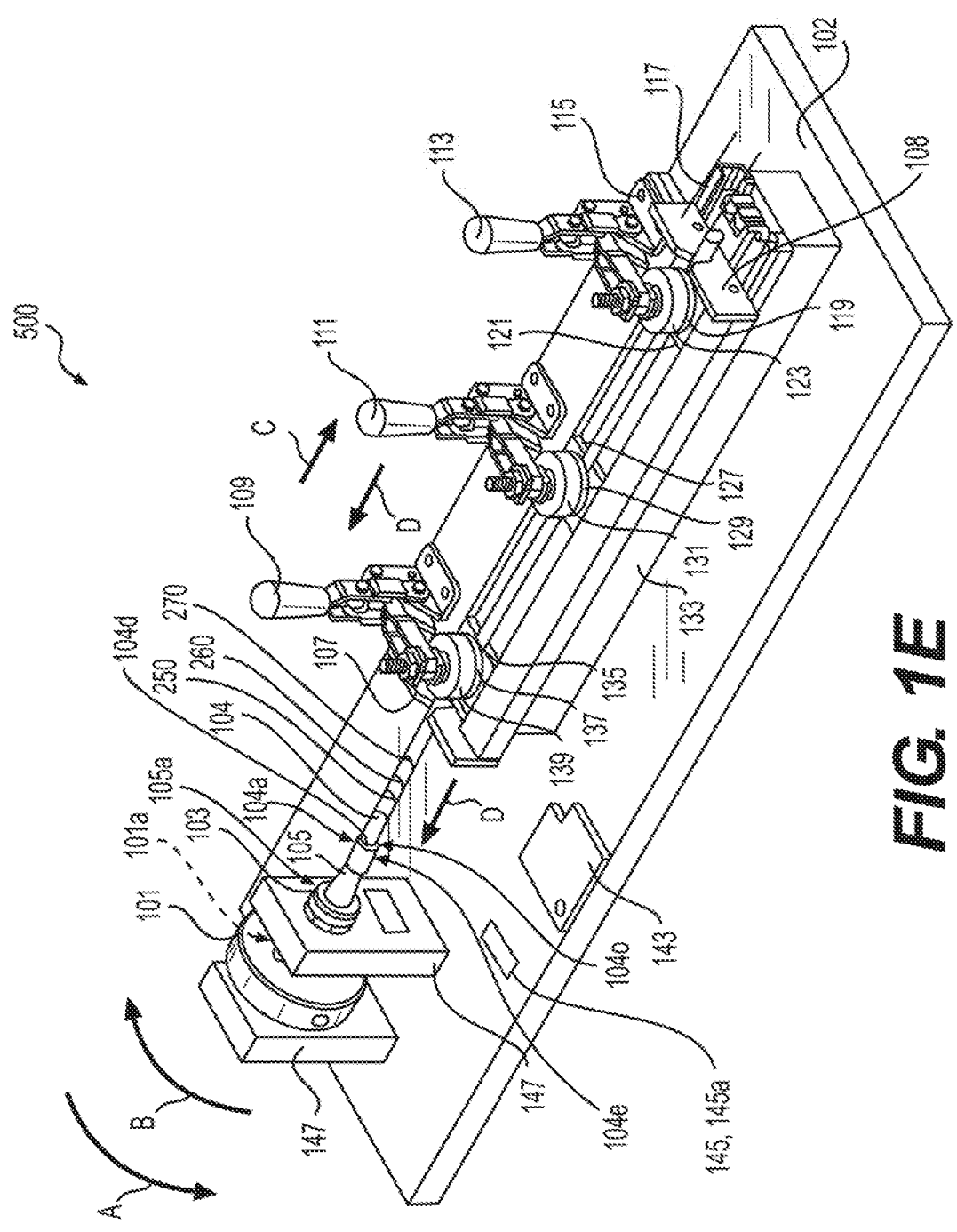
FIG. 1E is perspective view of FIG. 1C illustrating an embodiment of a material joining device, such as the flexi needle fixture device, of FIG. 1A, showing the joining process of a metal or ceramic sleeve or cap member to a tubular member, such as a plastic catheter, including the various components of the device, according to the present invention.

Referring now to FIG. 1E, there is illustrated an exemplary flexi-needle fixture assembly device or material joining device 500, similar to the material joining device 100 of FIG. 1A, illustrating an embodiment of a device, apparatus and process for forming a resultant product by the joining of a distal end 104*d* of the tubular member 104 with the metal or ceramic tip or cap member 104*a*, the tubular member 104 being positioned in and held by the positioning member 107 and being moved by the moveable carriage 115 in a direction toward and into an opening 104*o* in a distal end 104*e* of the metal or ceramic tip or cap member 104*a* while being held by the holding member 105*a* and while being rotated by communication with the rotation member 101 and the shaft assembly 101*a* to generate heat to melt or soften the portion of the distal end 104*d* to be fitted, joined or retained therein to form the resultant product without the use or addition of a synthetic or natural adhesive or other joining material in forming the bond to join the metal or ceramic sleeve or cap member 104*a* to or with the tubular member 104.

The material joining device 500 includes a base 102 having a setting or tube depth gauge 143 to measure tube dimensions, such as a tube diameter, to facilitate positioning and aligning the first and second materials for the joining process, a bearing block 147 holding a suitable collar 103, such as a PV collar, and pin vise 105 (mandrel piece) forming the holding member 105*a* coupled to a rotary application knob or rotation member 101 along the shaft assembly 101*a*, similar to that previously described. A slide mount 133 having the movable carriage 115 sliding over a drawer slide 117, having toggle clamps 111, 113 and 109 with clamp pucks 139, 131 and 123 resting on silicone pads 137, 129 and 119 attached over another silicone pad 135, 127 and 121 respectively is adapted to hold and position the tubular member 104 along a locator or positioning member 107 associated with the moveable carriage 115 so that the tubular member 104 can be joined and attached with the metal or ceramic sleeve or cap member 104a, similar to that previously described. The FIG. 1E material joining apparatus 500 illustrates exemplary embodiments of apparatus and process for attaching or joining the tubular member 104 with the metal or ceramic sleeve or cap member 104a being held by the holding member 105a including the mandrel or collar member 103 to form a composite joined product of a first material and a second material, such as a metal/polymeric composite joined product, for example. As described, the arrows A and B indicate respective rotation directions of the rotation member 101, and the arrows C and D indicate respective movement directions of the moveable carriage 115.

Figure 1F:
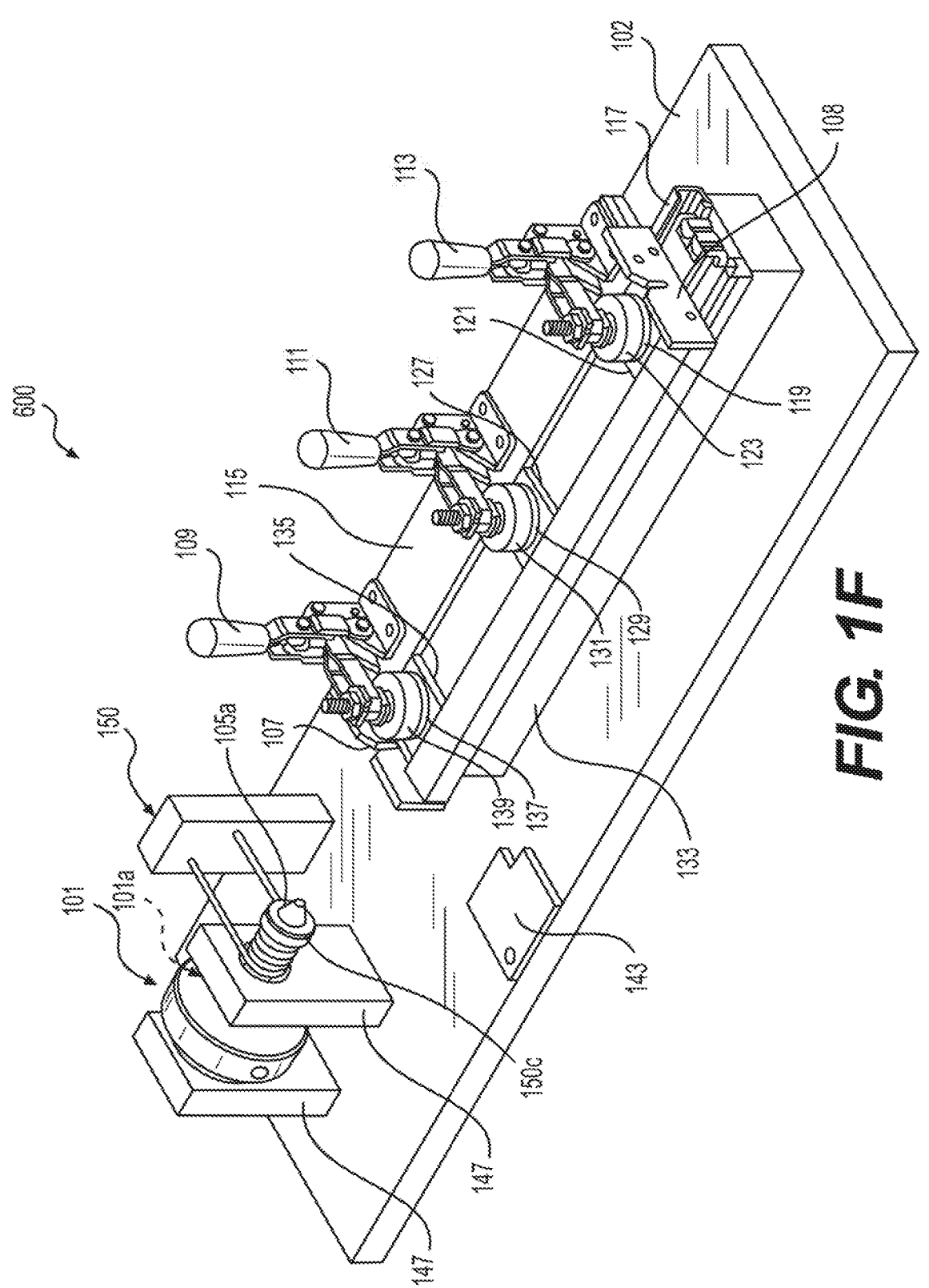
FIG. 1F is perspective view of FIG. 1C illustrating an embodiment of a material joining apparatus, such as the flexi needle fixture device, of FIG. 1A, showing a heating element, such as an induction or other type of heating elements, as can be used with the device, according to the present invention.

FIG. 1F illustrates an exemplary flexi-needle fixture assembly device or material joining device 600 similar to the material joining device 300 of FIG. 1C and is similar to the material joining device 100 of FIG. 1A. The material joining device 600 includes a rotary application knob or rotation member 101 and the shaft assembly 101a in communication with the holding member 105a, similar to that described. Also, the material joining device includes an induction or other type of suitable heater or heating device 150, as can be powered by the power 158 and controlled by the controller/processor 152, as described, for example, that is connected and can include a suitable clamp or spring type heating element 150c positioned in engaging or surrounding relation with at least a portion of the holding member 105a, such as a portion of the collar member 103 or a portion of the mandrel or pin vise 105 for delivering heat to the holding member 105a for transferring heat through the holding member 105a to the metal or ceramic sleeve or cap member 104a to transfer heat through or by the metal or ceramic sleeve or cap member 104a to the tubular member 104 to heat the tubular member 104 to its softening point, melting point or glass transition temperature ($T_g$) thereby transferring heat through or to the metal or ceramic sleeve or cap member 104a as needed to melt or soften the tubular member 104 when engaged with the metal or ceramic sleeve or cap member 104a during the fitting or joining process to soften a portion of the tubular member 104 to facilitate fitting, retaining and joining of the metal or ceramic sleeve or cap member 104a with the tubular member 104.

Also, for example, as described, the metal or ceramic sleeve or cap member 104a can be a sleeve or cap member 104a of a suitable first material having a first melting point, a first softening point or a first glass transition temperature, and the tubular member 104 can be a tubular member 104 of a suitable second material having a second melting point, a second softening point or a second glass transition temperature, and the second melting point, the second softening point or the second glass transition temperature of the second material being less than the respective first melting point, the first softening point or the first glass transition temperature of the first material, as can depend on the use or application, and should not be construed in a limiting sense.

Further, similar to that previously described, the material joining device 600 of FIG. 1F includes the tube depth gauge 143, a slide mount 133 having a movable carriage 115 sliding over a drawer slide 117, having the toggle clamps 111, 113 and 109 with the clamp pucks 139, 131 and 123 resting on silicone pads 137, 129 and 119 attached over another silicone pad 135, 127 and 121, respectively, adapted to hold and position a tubular member, such as the tubular member 104 of the second material, along a locator or positioning member 107 to be joined and attached with a sleeve or cap member of a metal, ceramic or other suitable first material, such as the metal or ceramic sleeve or cap member 104a. The FIG. 1F material joining apparatus 600 therefore similarly illustrates apparatus for use in exemplary embodiments of processes of attaching or joining the tubular member 104 of a second material with a sleeve or cap member 104a of a first material held and positioned on the mandrel or pin vise 105 of the holding member 105a to form a resultant composite joined product of a first material and a second material.

Referring now to FIGS. 2A1 and 2A2, FIG. 2A1 shows an exemplary embodiment of a resultant joined composite product J, such as a catheter, a flexi needle, or a plumbing, industrial or other type of joined component J. The joined component J includes a sleeve or cap member 104a of a first material, as described, such as a metallic, ceramic or polymeric sleeve or cap member 104a, and a tubular member 104 of a second material, as described, such as a plastic, biocompatible plastic, or polymeric tubular member 104. FIG. 2A2 shows an exemplary embodiment of the disassembled component J of FIG. 2A1, having the sleeve or cap member 104a and the tubular member 104, as described. Also, the shape, configuration and dimensions of the sleeve or cap member 104a of the first material and of the tubular member 104 of the second material are each not limited to that described and can each be of various suitable shapes, configurations and dimensions, such as square, rectangular, triangular, pentagonal, hexagonal, octagonal, cylindrical, spherical, or combinations thereof, as can depend on the use or application, and should not be construed in a limiting sense.

FIGS. 2B1 and 2B2 illustrate cross-sectional views of an embodiment of a flexi needle F having a sleeve or cap member 220 of a suitable first material, such as a metal or ceramic material, and of a suitable configuration, shape or diameter, and having a proximal end 230 and a distal end portion 235. The distal end portion 235 of the sleeve or cap member 220 has an opening 235a of a suitable configuration, shape or diameter adapted to receive within the opening 235a a proximal end portion 240 of a tubular member 200 of a suitable second material, such as a biocompatible plastic, plastic or polymeric material, and of a suitable configuration, shape or diameter. The proximal end portion 240 of a tubular member 200 can have an opening 240a of a suitable configuration, shape or diameter. Also, the tubular member 200 can have a tip 210 with a small opening 210a in the distal position, such as illustrated in FIG. 2B2. Typically, the outer diameter of the tubular plastic member 200, such as when used for a flexi needle is in the range of from about 1 mm to about 5 cm and the length of the tubular member 200, such as when used for a flexi needle, is between about 1 cm to about 100 cm, for example. Similarly, the outer diameter of the metal or ceramic sleeve or cap member 220, such as when used for a flexi needle, is in the range of from about 1 mm to about 5 cm and the length is between about 1 cm to 10 cm, for example. The interior surface of the sleeve or cap member 220 can be smooth or corrugated or rough, as dependent on the use or application, for example. Also, the tubular member 200 has position markers 250, 260 and 270 along the tubular member 200 to facilitate an accurate length the tubular member 200 in the final resultant product and/or placement or positioning of the resultant joined product during its use.

FIGS. 2C1 and 2C2 shows the cross-sectional view of an embodiment of a flexi needle G, similar to the flexi needle F of FIGS. 2B1 and 2B2. However, in the resultant product G, the distal end 235 of the sleeve or cap member 220 having the opening 235a is positioned within the opening 240a and is positioned and retained within the proximal end 240 of the tubular member 200. In the joining process to form the resultant product G, heat generated by frictional engagement of the sleeve or cap member 220 with tubular member 200 and/or that is transmitted through the sleeve or cap member 220 facilitates softening or melting a portion of the tubular member 200, such as its proximal end portion 240, that is in engaging relation with the sleeve or cap member 220 thereby facilitating forming a bond joining these components together in forming the resultant joined product G.

Also, similar to the resultant product F, typically, the outer diameter of the tubular plastic member 200, such as when used for a flexi needle, is in the range of from about 1 mm to about 5 cm and the length of the tubular member 200, such as when used for a flexi needle, is between about 1 cm to about 100 cm, for example. Similarly, in the resultant joined product G, the outer diameter of the metal or ceramic sleeve or cap member 220, such as when used for a flexi needle, is in the range of from about 1 mm to about 5 cm and the length is between about 1 cm to 10 cm, for example. Also, in the resultant product G, the exterior surface of the sleeve or cap member 220 can be smooth or corrugated or rough, as dependent on the use or application, for example, to facilitate joining of the components of the resultant product G. Also, the tubular member 200 has the position markers 250, 260 and 270 along the tubular member 200 to facilitate an accurate length the tubular member 200 in the final resultant product and/or placement or positioning of the resultant joined product during its use.

In embodiments, the tubular member 200 can be flexible, rigid or semi-rigid in construction and can be made various suitable materials, such as of a polymeric material such as polyurethane, polyethylene, polymethyl methacrylate (PMMA), polycarbonate, styrenic block copolymers, poly-butylene terephthalate (PBT), Teflon, Nylon, PVC, among other examples and materials, as can depend on the use or application, and should not be construed in a limiting sense. Also, in embodiments, the sleeve or cap member 220 can be flexible, rigid or semi-rigid in construction and can be made various suitable materials, such as metal, ceramic or poly-meric or plastic materials, as can depend on the use or application, and should not be construed in a limiting sense.

FIGS. 2D1-2D4 shows an exemplary embodiment of a process of joining a metal or ceramic sleeve or cap member 222 with a tubular member 221. In the first step in FIG. 2D1, the metal or ceramic sleeve or cap member 222 and the tubular plastic member 221 having a position marker 203, similar to the position markers 250, 260 and 270, are positioned in facing relation to each other for engagement. FIG. 2D2 shows a progression of the joining process as the metal or ceramic sleeve or cap member 222 is brought into engaging relation with an end portion of the tubular plastic member 221 that is being inserted into an opening in the metal or ceramic sleeve or cap member 222 up to a prede-termined distance marked "d1". FIG. 2D3 shows a cross-sectional view of a further progression of the joining process as the tubular plastic member 221 is being inserted into the opening or open portion of the metal or ceramic sleeve or cap member 222 showing the melted or softened plastic 205 of a portion of the tubular member 221 engaged with a portion of the metal or ceramic sleeve or cap member 222 resulting from the transmitted or generated heat of a length of 'd2" inside the metal or ceramic sleeve or cap member 222. FIG. 2D4 shows the resultant joined composite product K having the plastic of the tubular plastic member 221 being fully inserted to the predetermined distance "d1" into the metal or ceramic sleeve or cap portion 222 and being bonded with the metal or ceramic sleeve or cap portion 222 forming the resultant composite joined product K.

Figure 2E:
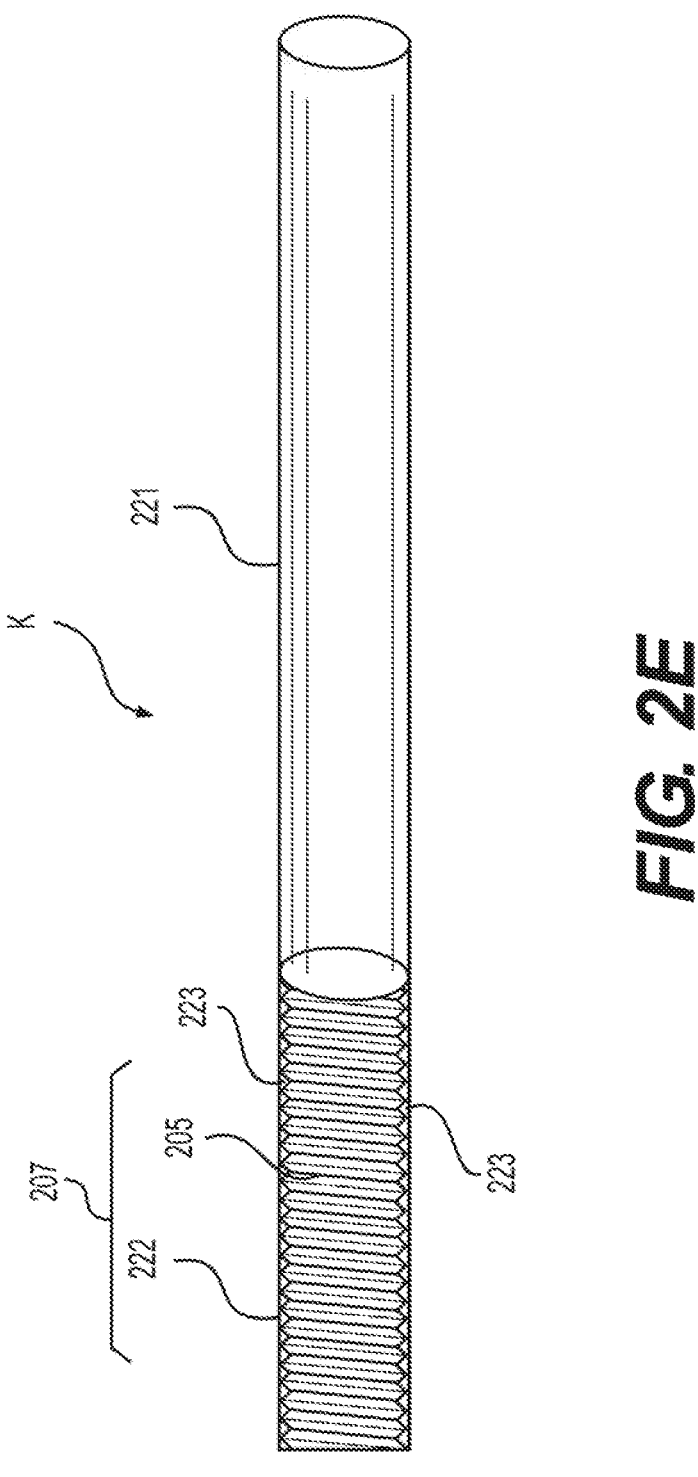
FIG. 2E shows an embodiment of the tubular member joined with the metal or ceramic tip or cap member having a melted plastic of the tubular member inside the metal or ceramic tip or cap member, according to the present invention.
Figure 3:
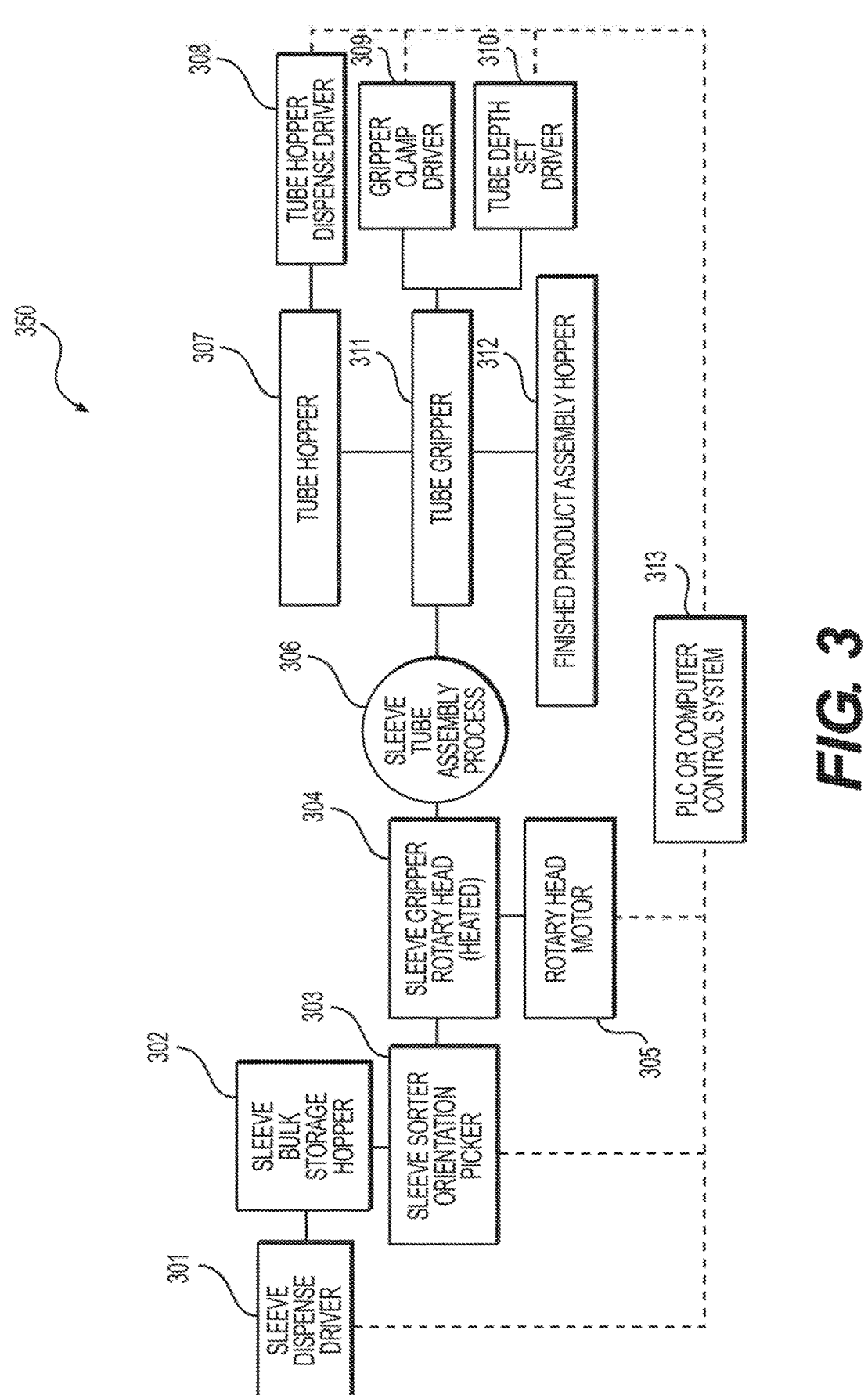

Referring now to FIG. 2E, there is shown a cross-sectional view of an embodiment of the resultant joined composite product K formed by the metal or ceramic sleeve or cap member 222 having the melted and/or softened plastic 205 of the tubular plastic member 221 that has cooled and adhered to an inside surface 223 of a distal end 207 of the metal or ceramic sleeve or cap member 222 due to the insertion of the tubular plastic member 221 into the metal or ceramic sleeve or cap member 222 and rotation steps generating or transmitting heat as the tubular plastic member 221 continues to engage and be joined with the metal or ceramic sleeve or cap member 222 to form the composite joined product, such as the joined composite product K. Also, the inside surface of ceramic sleeve or cap member 222 can have a smooth grooved, rough or corrugated sur-face, with a grooved or corrugated inside surface being indicated by the numeral 223, such rough, grooved or corrugated inside surface 223 can facilitate the bonding of the sleeve or cap member 222 with the tubular plastic member 221, for example.

Referring to FIG. 3, a block diagram illustration of an exemplary embodiment of an automated and mechanized flexi needle fixture device or material joining device or assembly system or apparatus 350 having components equivalent to or performing functions substantially equiva-lent to those performed by described exemplary embodi-ments of the material joining devices 100-600 of FIGS. 1A-1F, as described. In the automated mode of the flexi-needle assembly device or material joining device 350, the following steps are conducted by the corresponding appa-ratus. In the material joining apparatus 350, a tube hopper 307 is loaded with pre-cut-to-length tubes positioned with a pointed end toward a tube depth set driver 310 that deter-mines or measures a tube depth. Next, a sleeve bulk storage hopper 302 is loaded with the sleeve or cap member to be fitted over the tube member. For the operation, a single sleeve or cap member is dispensed to a sleeve sorter orien-tation picker 303 and the sleeve sorter orientation picker 303 inspects the sleeve or cap member to determine a location of its large open end. If the open end of the sleeve or cap member is positioned incorrectly, the orientation routine of the sleeve sorter orientation picker 303 flips it around. If correctly positioned, the sleeve sorter orientation picker 303 sets the sleeve or cap member into a sleeve gripper rotary head 304 at a pre-determined depth. A clamp member of the sleeve gripper rotary head 304 grips the sleeve or cap member and an integral heater of the sleeve gripper rotary head 304 heats the sleeve or cap member to the desired or a predetermined temperature.

As to the tubular member to be joined with the sleeve or cap member, in the exemplary automated material joining device 350, typically a single tubular member from a tube hopper 307 is dispensed into a tube gripper 311 assembly by a tube hopper dispense driver 308. A tube depth set driver 310 pushes the tubular member to set an exposure of 1 cm, for example, or other suitable exposure, to the assembly process side. A tube gripper clamp driver 309 activates to grip the tubular member firmly. In the assembly stage in a sleeve tube assembly process 306 section of the material joining device 350, the sleeve gripper rotary head 304, driven by a rotary head motor 305, begins to rotate counter clock wise (facing the open end of the sleeve or cap member). The tube depth set driver 310 presses the tube gripper assembly 311 introducing the exposed tubular mem-ber to the rotating sleeve or cap member. Upon contact of the tubular member with the inside of the sleeve or cap member (the sleeve or cap member can have threads, for example, on a portion of its open, interior surface to facilitate the joining of the composite materials), the sleeve gripper rotary head 304 continues to rotate thus engaging, such as by screwing, the tubular member into the sleeve or cap member until the depth sensor is satisfied (such as a 1 cm depth for a flexi needle, for example). Upon completion of the joining process, the sleeve gripper rotary head 304 stops rotating, and a rotary head grip of the sleeve gripper rotary head 304 opens, and then the tube depth set driver 310 extracts the joined sleeve or cap member/tubular member assembly from the sleeve gripper rotary head 304. The tube gripper clamp driver 309 releases the tube/sleeve assembly and flips it into a finished product assembly hopper 312. The various components and elements of the material joining device and the control of the material joining process are under control of a suitable controller/processor system, such as a PLC or Computer Control System 313, similar to that described in relation to the material joining device 400 of FIG. 1D. The material joining process in the material joining device 350 can be repeated, as desired, to form a predetermined number of resultant joined products.

In the above-described sleeve tube assembly process in the material joining device 350, the sleeve dispense driver 301 is operably connected to the sleeve bulk storage hopper 302, which is associated with the sleeve sorter orientation picker 303, which is operably connected to the sleeve gripper rotary head 304 that may optionally be heated by a heater associated with the sleeve gripper rotary head 304, which is in turn associated with the rotary head motor 305 that drives the sleeve gripper rotary head 304. The tube hopper 307 is operably connected with the tube hopper dispense driver 308 and the tube gripper 311. The tube gripper 311 is operably connected to the gripper clamp driver 309 and the tube depth set driver 310. All these components and parts of the material joining device 350 can be configured to be operated by a computer control system, such as the PLC or Computer Control System 313, to operate and control the above described composite material joining process, such as in joining a sleeve or cap member and a tubular member, as described. Also, the above described components of the automated material joining apparatus 350, such as the described hoppers, grippers, drivers, motors, computers, processors etc., can be implemented from similar components known in the art when taken in conjunction with the novel teachings, description and drawings provided herein of the instant disclosure and application to arrive at embodiments of the described material joining device or apparatus and material joining process.

As a first example, referring to FIG. 4A, an embodiment of a process or method for preparing a metal or ceramic sleeve or cap member fitted or joined with a tubular plastic member is shown and described using a block diagram of a joining process 700. In the process 700, the process begins at step 701 of selecting a tubular plastic member and a metal/ceramic cap member to be securely joined to a distal end of the tubular plastic member. The process 700 then proceeds to step 702 of placing the metal/ceramic cap member in engaging relation with a holding member of the material joining device.

The process 700 then proceeds to step 703 of securing the tubular plastic member on a locator/positioner (positioning member) of the material joining device and positioning a distal end of the tubular plastic member in engaging relation with an end of the metal/ceramic cap member positioned in the holding member. The process 700 then proceeds to step

704 of rotating the holding member and maintaining the tubular plastic member in frictionally engaging relation with the metal/ceramic cap member to melt or soften a predetermined portion of the distal end of the tubular plastic member engaged with the metal/ceramic cap member to integrally join the predetermined portion of the distal end of the tubular plastic member within the metal/ceramic cap member forming a mechanically joined composite member. Optionally, the process 700 can include an additional step 705 of optionally heating the metal/ceramic cap member to increase the temperature of the predetermined portion of the tubular plastic member positioned in engaging relation with the metal/ceramic cap member to facilitate heating/softening the predetermined portion of the tubular plastic member in forming the mechanically joined composite member. The process 700 can then return to step 701 to form another resultant joined composite product or can then proceed to end.

As a second example, referring to FIG. 4B, an embodiment of a process or method for preparing a metal or ceramic sleeve or cap member fitted or joined with a tubular plastic member is shown and described using a block diagram of a joining process 800. In the process 800, the process begins at step 811 of selecting a tubular flexible catheter and a metal/ceramic cap member to be securely joined to a distal end of the catheter. The process 800 then proceeds to step 812 of placing the metal/ceramic cap member in engaging relation with a holding member of the material joining device. The process 800 then proceeds to step 813 of securing the tubular flexible catheter on a locator/positioner (positioning member) of the material joining device and positioning a distal end of the tubular flexible catheter in engaging relation with an end of the metal/ceramic cap member positioned in the holding member.

The process 800 then proceeds to step 814 of rotating the holding member and maintaining the flexible catheter in frictionally engaging relation with the metal/ceramic cap member to melt or soften a predetermined portion of the distal end of the tubular flexible catheter engaged with the metal/ceramic cap member to integrally join the predetermined portion of the distal end of the tubular flexible catheter within the metal/ceramic cap member forming a mechanically joined composite member. Optionally, the process 800 can include the additional step 815 of optionally heating the metal/ceramic cap member to increase the temperature of the predetermined portion of the tubular flexible catheter positioned in engaging relation with the metal/ceramic cap member to facilitate heating/softening the predetermined portion of the tubular flexible catheter, such as heating the tubular flexible catheter at least up to the glass transition temperature (Tg) of the tubular plastic catheter, in forming the mechanically joined composite member. The process 800 can then return to step 811 to form another resultant joined composite product or can then proceed to end.

Embodiments of the metal/ceramic tubular catheter composite product can include wires or other radioactive source or pellets positioned inside the product, the wires, pellets or source having radioactivity for treatment in malignant tissues, such as in treating malignancies in the prostrate and breast, for example. Also, embodiments of the material joining device for joining a metal or ceramic sleeve or cap member with a tubular member as described herein can be advantageous in that the joined resultant product can be formed without the addition of any natural or synthetic adhesive material in the joining process, but, rather, can selectively employ one or more of mechanical force, friction and/or heat to soften or melt the plastic over or within the metal/ceramic piece or cap member to join these components or, more generally, to join first and second member components of first and second materials, providing a relatively secure bond, as described. Another advantage of embodiments of a material joining process and of embodiments of material joining apparatus is that the device or process is amenable to a large scale automated commercial production, for example.

Further, in various medical applications and treatments, there has been a need for a metal tubular member composite that can address a problem of the metal or ceramic tip coming off during a patient treatment, and it is believed that embodiments of the joined composite resultant product, by providing a relatively secure bond, promote addressing this need. While the invention is contemplated for medical use, it is not limited thereto and the composite joined resultant product of a sleeve or cap member joined to a tubular member and the material joining devices to manufacture the composite product could be used for various other applications, such as in veterinary or other biological diagnoses and treatments, as well as can have applicability in the construction and pipe industry and in other device or industrial applications, and, as such, should not be construed in a limiting sense.

It is to be understood that the present invention is not limited to the embodiments described above, but encompasses any and all embodiments within the scope of the following claims.

We claim:

1. A material joining device for joining a first member of a first material to a second member of a second material, comprising:

a base;

a rotatable shaft assembly communicatively associated with the base, the rotatable shaft assembly having a holding member rotatable with the shaft assembly, the holding member adapted to receive and hold the first member of the first material having a first glass transition temperature, a first melting point or a first softening point, the first member comprising a ceramic material or a metal material;

a moveable carriage communicatively associated with the base, the moveable carriage including a positioning member, the positioning member configured to position and hold the second member of the second material having a second glass transition temperature, a second melting point or a second softening point, the second glass transition temperature, the second melting point or the second softening point being less than the first glass transition temperature, the first melting point or the first softening point, respectively, and the moveable carriage configured to selectively move to position the second member in engaging relation with the first member; and a heater communicatively associated with the holding member to selectively generate and transfer heat to the holding member and through the first member to a portion of the second member when in engaging relation with the first member to selectively heat, to increase a temperature of, the portion of the second member when in engaging relation with the first member to at least the second melting point, the second softening point, or the second glass transition temperature to facilitate melting or softening the portion of the second member when engaged with the first member without melting or softening the first member to facilitate bonding the second member with the first member, wherein the second material of the second member comprises a plastic material or a polymeric material and rotation of the holding member in complete revolutions at a given rotational speed without oscillatory or orbital motion and positioning of the movable carriage to maintain the second member in engaging relation with the first member frictionally engages the first member with the second member generating frictional heat to melt or soften the portion of the second member when in engaging relation with the first member without melting or softening the first member bonding the second member to the first member forming a composite joined product without addition of an adhesive.

2. The material joining device according to claim 1, wherein:

the first member comprises a sleeve or a cap member, the second member comprises a tubular member, and the plastic material is a biocompatible plastic material.

3. The material joining device according to claim 1, wherein:

the metal material of the first member is selected from the group consisting of titanium, steel, tungsten, tin, copper, bronze, gold, platinum, silver and an alloy thereof, the plastic material comprises a biocompatible plastic material, and the polymeric material is selected from the group consisting of polyurethane, polyethylene, polymethyl methacrylate (PMMA), polycarbonate, styrenic block copolymers, polybutylene terephthalate (PBT), Nylon, and poly vinyl chloride (PVC).

4. The material joining device according to claim 1, wherein:

the composite joined product is a flexi-needle or a catheter, the first member comprises a sleeve or a cap member, and the second member comprises a flexible tubular member.

5. The material joining device according to claim 4, wherein:

an outer diameter of the tubular member is in a range of from about 1 mm to about 5 cm and a length of the tubular member is between about 1 cm to about 100 cm, and an outer diameter of the sleeve or the cap member is in a range of from about 1 mm to about 5 cm and a length of the sleeve or the cap member is between about 1 cm to about 10 cm.

6. The material joining device according to claim 1, wherein:

the first member is a sleeve or a cap member, and the second member is a flexible plastic catheter.

7. The material joining device according to claim 1, wherein:

the heater includes at least one of a heater collar member or a spring or clamp type heating element configured to surround at least a portion of the holding member.

8. A material joining device for joining a sleeve or a cap member with a tubular member, comprising:

a base comprising a bearing block including a shaft assembly associated with a holding member, the holding member adapted to hold or support the sleeve or the cap member and including one or more of a collar member, a mandrel or a pin vise, the mandrel or the pin vise having an end portion adapted to hold or support the sleeve or the cap member to be joined with the tubular member, the sleeve or the cap member comprising a metal material or a ceramic material and the tubular member comprising a plastic material or a polymeric material;

a moveable carriage communicatively associated with the base, the movable carriage positioned in communication with the base, the movable carriage being configured to reciprocally move in a direction toward or a direction away from the holding member, and the movable carriage including a positioning member configured to hold the tubular member to be joined with the sleeve or the cap member;

a heater communicatively associated with the holding member to selectively generate and transfer heat to the holding member and through the sleeve or the cap member to the tubular member to selectively heat, to increase a temperature of, a portion of the tubular member when in engaging relation with the sleeve or the cap member to facilitate melting or softening the portion of the tubular member when in engaging relation with the sleeve or the cap member without melting or softening the sleeve or the cap member to facilitate bonding the tubular member to the sleeve or the cap member;

a carriage driver including a first motor or a manual driver member operatively coupled with the moveable carriage to selectively move the moveable carriage towards or away from the holding member; and a rotation driver including a second motor or a manual rotation member operatively coupled to the shaft assembly configured to rotate the holding member around a linear axis of the shaft assembly, wherein rotation of the holding member in complete revolutions at a given rotational speed without oscillatory or orbital motion and positioning of the movable carriage to maintain the tubular member in engaging relation with the sleeve or the cap member frictionally engages the sleeve or the cap member with the tubular member generating frictional heat to melt or soften the portion of the tubular member when in engaging relation with the sleeve or the cap member without melting or softening the sleeve or the cap member bonding the tubular member to the sleeve or the cap member forming a composite joined product without addition of an adhesive.

9. The material joining device according to claim 8, wherein:

the heater includes at least one of a heater collar member or a spring or clamp type heating element configured to surround at least a portion of the holding member to facilitate heating the portion of the tubular member when in engaging relation with the sleeve or the cap member to at least its softening point, melting point or glass transition temperature to facilitate melting or softening the portion of the tubular member when engaged with the sleeve or the cap member to facilitate bonding the tubular member with the sleeve or the cap member.

10. The material joining device according to claim 8, wherein:

the metal material is selected from the group consisting of titanium, steel, tungsten, tin, copper, bronze, gold, platinum, silver and an alloy thereof, the plastic material is a biocompatible plastic material, and the polymeric material is selected from the group consisting of polyurethane, polyethylene, polymethyl methacrylate (PMMA), polycarbonate, styrenic block copolymers, polybutylene terephthalate (PBT), Nylon, and poly vinyl chloride (PVC).

11. The material joining device according to claim 8, further comprising:

a drawer slide communicatively associated with the base and the moveable carriage for sliding the moveable carriage forward toward or rearward from the holding member.

12. The material joining device according to claim 8, further comprising:

a sensor to sense one or more of a moved distance, a position marker or a change in position of the tubular member when positioned on the moveable carriage to control a length of the tubular member joined with the sleeve or the cap member or to control a length of the tubular member in the composite joined product.

13. The material joining device according to claim 8, further comprising:

a measurement device for determining a moved distance of the tubular member during joining of the tubular member with the sleeve or the cap member.

14. The material joining device according to claim 8, further comprising:

a controller/processor for controlling one or more of the carriage driver, the rotation driver and the heater, the controller/processor selectively controlling the heater to selectively control the heat generated by the heater to selectively heat the portion of the tubular member when in engaging relation with the sleeve or the cap member.

15. The material joining device according to claim 14, further comprising:

a user interface display operatively associated with the controller/processor.

16. A composite joined product formed by a process comprising:

selecting a first member of a first material having a first glass transition temperature, a first melting point or a first softening point, the first material comprising a ceramic material or a metal material;

selecting a second member of a second material to be joined to the first member, the second member of the second material having a second glass transition temperature, a second melting point or a second softening point, the second glass transition temperature, the second melting point or the second softening point being less than the first glass transition temperature, the first melting point or the first softening point, respectively, and the second material comprising a plastic material or a polymeric material;

placing the first member in engaging relation with a holding member, the holding member adapted to receive and hold the first member;

placing the first member in engaging relation with the second member;

selectively heating the holding member by a heater communicatively associated with the holding member to selectively generate and transfer heat from the heater to the holding member and through the first member to the second member to selectively heat, to increase a temperature of, a predetermined portion of the second member to at least the second melting point, the second softening point, or the second glass transition temperature to facilitate melting or softening the predetermined portion of the second member engaged with the first member without melting of softening the first member to facilitate bonding the second member with the first member; and rotating the first member in complete revolutions at a given rotational speed without oscillatory or orbital motion and maintaining the second member in frictionally engaging relation with the first member generating frictional heat to melt or soften the predetermined portion of the second member engaged with first member without melting or softening the first member to integrally join a predetermined portion of the first member with the second member forming the composite joined product without addition of an adhesive.

17. The composite joined product formed by the process according to claim 16, wherein:

the first member comprises a sleeve or a cap member, the second member comprises a tubular member, and the plastic material is a biocompatible plastic material.

18. The composite joined product formed by the process according to claim 16, wherein:

the metal material is selected from the group consisting of titanium, steel, tungsten, tin, copper, bronze, gold, platinum, silver and an alloy thereof, the plastic material comprises a biocompatible plastic material, and the polymeric material is selected from the group consisting of polyurethane, polyethylene, polymethyl methacrylate (PMMA), polycarbonate, styrenic block copolymers, polybutylene terephthalate (PBT), Nylon, and poly vinyl chloride (PVC).

19. The composite joined product formed by the process according to claim 18, wherein:

the composite joined product is a flexi-needle or a catheter.

20. A method for forming a composite joined product, comprising the steps of:

selecting a first member of a first material having a first glass transition temperature, a first melting point or a first softening point, the first material comprising a ceramic material or a metal material;

selecting a second member of a second material to be joined to the first member, the second member of the second material having a second glass transition temperature, a second melting point or a second softening point, the second glass transition temperature, the second melting point or the second softening point being less than the first glass transition temperature, the first melting point or the first softening point, respectively, and the second material comprising a plastic material or a polymeric material;

placing the first member in engaging relation with a holding member, the holding member adapted to receive and hold the first member;

placing the first member in engaging relation with the second member;

selectively controlling heating the holding member by a heater communicatively associated with the holding member to selectively generate and transfer heat from the heater to the holding member and through the first member to the second member to selectively heat, to increase a temperature of, a predetermined portion of the second member engaged with the first member to heat the predetermined portion of the second member to at least the second melting point, the second softening point, or the second glass transition temperature to facilitate melting or softening the predetermined portion of the second member engaged with the first member without melting or softening the first member to facilitate bonding the second member with the first member; and rotating the first member in complete revolutions at a given rotational speed without oscillatory or orbital motion and maintaining the second member in frictionally engaging relation with the first member generating frictional heat to melt or soften the predetermined portion of the second member engaged with the first member without melting or softening the first member to integrally join a predetermined portion of the first member with the second member forming the composite joined product without addition of an adhesive.

21. The method for forming a composite joined product according to claim 20, wherein:

the composite joined product is a flexi-needle or a catheter.

22. The method for forming a composite joined product according to claim 21, wherein:

the metal material of the first member is selected from the group consisting of titanium, steel, tungsten, tin, copper, bronze, gold, platinum, silver and an alloy thereof, the plastic material comprises a biocompatible plastic material, and the polymeric material is selected from the group consisting of polyurethane, polyethylene, polymethyl methacrylate (PMMA), polycarbonate, styrenic block copolymers, polybutylene terephthalate (PBT), Nylon, and poly vinyl chloride (PVC).

23. A method for forming a composite joined product, comprising the steps of:

selecting a tubular member and a sleeve or a cap member to be joined to the tubular member, the tubular member formed of a material comprising a plastic material or a polymeric material and the sleeve or the cap member comprising a metal material or a ceramic material;

placing the sleeve or the cap member in engaging relation with a holding member of a material joining device;

securing the tubular member on a positioning member of the material joining device;

positioning an end portion of the tubular member secured on the positioning member in engaging relation with an end portion of the sleeve or the cap member positioned in the holding member;

selectively heating the holding member by a heater to selectively generate and transfer heat from the heater to the holding member and through the end portion of the sleeve or the cap member to the end portion of the tubular member engaged with the end portion of the sleeve or cap member to selectively heat, to increase a temperature of, a predetermined portion of the end portion of the tubular member to at least a melting point, a softening point, or a glass transition temperature of the material comprising the tubular member in forming the composite joined product to facilitate melting or softening the predetermined portion of the end portion of the tubular member without melting or softening the sleeve or the cap member to facilitate joining the tubular member to the sleeve or the cap member; and rotating the holding member in complete revolutions at a given rotational speed without oscillatory or orbital motion and maintaining the tubular member secured on the positioning member in frictionally engaging relation with the sleeve or the cap member generating frictional heat to melt or soften the predetermined portion of the end portion of the tubular member engaged with the end portion of the sleeve or the cap member without melting or softening the sleeve or the cap member to integrally join the predetermined portion of the end portion of the tubular member with the
sleeve or the cap member forming the composite joined
product without use of an adhesive.

24. The method for forming a composite joined product
according to claim 23, wherein:

the composite joined product is a flexi-needle or a cath-
eter.

25. The method for forming a composite joined product
according to claim 24, wherein:

the metal material is selected from the group consisting of
titanium, steel, tungsten, tin, copper, bronze, gold,
platinum, silver and an alloy thereof, the plastic material comprises a biocompatible plastic
material, and the polymeric material is selected from the group con-
sisting of polyurethane, polyethylene, polymethyl
methacrylate (PMMA), polycarbonate, styrenic block
copolymers, polybutylene terephthalate (PBT), Nylon,
and poly vinyl chloride (PVC).

\* \* \* \* \*